United States Patent
Shmilovich et al.

(10) Patent No.: US 11,033,898 B2
(45) Date of Patent: Jun. 15, 2021

(54) FLUIDIC MICROELECTROMECHANICAL SENSORS/DEVICES AND FABRICATION METHODS THEREOF

(71) Applicant: EZMEMS LTD., Netanya (IL)

(72) Inventors: Tsvi Shmilovich, Pardes Hanna-Karkur (IL); Nicola Molinazzi, Kfar Sava (IL)

(73) Assignee: EZMEMS LTD., Netanya (IL)

( * ) Notice: Subject to any disclaimer, the term of this patent is extended or adjusted under 35 U.S.C. 154(b) by 174 days.

(21) Appl. No.: 16/323,068

(22) PCT Filed: Aug. 1, 2017

(86) PCT No.: PCT/IL2017/050851
§ 371 (c)(1),
(2) Date: Feb. 4, 2019

(87) PCT Pub. No.: WO2018/025264
PCT Pub. Date: Feb. 8, 2018

(65) Prior Publication Data
US 2019/0160462 A1   May 30, 2019

Related U.S. Application Data

(63) Continuation-in-part of application No. 15/227,278, filed on Aug. 3, 2016, now Pat. No. 10,350,593.

(51) Int. Cl.
*G01L 9/00* (2006.01)
*G01L 19/00* (2006.01)
(Continued)

(52) U.S. Cl.
CPC ......... *B01L 3/502715* (2013.01); *A61M 5/31* (2013.01); *B01L 3/502707* (2013.01);
(Continued)

(58) Field of Classification Search
CPC ..... G01F 1/34; G01F 1/36; G01L 7/08; G01L 9/00–06; G01L 19/00; G01L 19/0007;
(Continued)

(56) References Cited

U.S. PATENT DOCUMENTS

| 4,227,151 A | 10/1980 | Ellis et al. |
| 4,398,542 A | 8/1983 | Cunningham et al. |

(Continued)

FOREIGN PATENT DOCUMENTS

| CN | 101815933 A | 8/2010 |
| CN | 103185612 A | 7/2013 |

(Continued)

OTHER PUBLICATIONS

Engel, et al., Multi-Layer Embedment of Conductive and Non-Conductive PDMS for All-Elastomer MEMS, Proceedings IEEE MEMS, 2006, XP 008148244, pp. 1-4.

(Continued)

*Primary Examiner* — Nguyen Q. Ha
(74) *Attorney, Agent, or Firm* — Browdy and Neimark, P.L.L.C.

(57) ABSTRACT

Structure and assembly of fluidic sensor devices are disclosed. A fluid sensor in some possible embodiments comprises a unitary/monolithic base body structure, or a base body structure assembled from two or more separate body elements configured to attach one to the other, and the base body structure having a fluid channel passing along the base body structure, an opening formed in said base body structure and fluidly communicating with the channel, and a sealing element comprising one or more sensing elements patterned thereon and sealably attached over the at least one opening such that its one or more sensing elements become located over the at least one opening.

18 Claims, 19 Drawing Sheets

(51) Int. Cl.
*A61M 5/31* (2006.01)
*B01L 3/00* (2006.01)
*G01L 9/04* (2006.01)
*B81B 7/00* (2006.01)
*B81C 1/00* (2006.01)
*G01F 1/34* (2006.01)
*G01F 1/36* (2006.01)

(52) U.S. Cl.
CPC ........ *B81B 7/0061* (2013.01); *B81C 1/00309* (2013.01); *G01L 9/04* (2013.01); *G01L 19/0007* (2013.01); *A61M 2205/0244* (2013.01); *A61M 2205/3327* (2013.01); *A61M 2207/00* (2013.01); *B01L 2200/0684* (2013.01); *B01L 2200/0689* (2013.01); *B01L 2300/0645* (2013.01); *B01L 2300/0887* (2013.01); *B01L 2300/0893* (2013.01); *B01L 2400/086* (2013.01); *B81B 2201/0264* (2013.01); *B81B 2203/0315* (2013.01); *B81B 2203/0338* (2013.01); *B81B 2207/094* (2013.01); *G01L 2019/0053* (2013.01)

(58) Field of Classification Search
CPC .. G01L 19/14; G01L 2019/0053; A61M 5/31; A61M 2205/0244; A61M 2205/3327; A61M 2207/00; B01L 3/502707; B01L 2200/0684; B01L 2200/0689; B01L 2300/0645; B01L 2300/0887; B01L 2400/086; B81B 7/0061; B81B 2201/0264; B81B 2203/0315; B81B 2203/0338; B81B 2207/094; B81C 1/00309
See application file for complete search history.

(56) References Cited

U.S. PATENT DOCUMENTS

| | | | |
|---|---|---|---|
| 5,848,971 A | 12/1998 | Fowler et al. | |
| 6,247,369 B1 | 6/2001 | Chapman et al. | |
| 6,782,755 B2 | 8/2004 | Tai et al. | |
| 6,857,449 B1 | 2/2005 | Chow | |
| 7,108,354 B2 | 9/2006 | Gulvin et al. | |
| 7,246,524 B1 | 7/2007 | Kholwadwala et al. | |
| 7,250,775 B1 | 7/2007 | Collins et al. | |
| 7,290,454 B2* | 11/2007 | Liu | G01L 9/00 |
| 7,291,126 B2 | 11/2007 | Shekalim | |
| 7,311,693 B2 | 12/2007 | Shekalim | |
| 7,318,351 B2 | 1/2008 | Cobianu et al. | |
| 7,375,404 B2 | 5/2008 | Park et al. | |
| 7,377,907 B2 | 5/2008 | Shekalim | |
| 9,283,319 B2* | 3/2016 | Geipel et al. | A61M 5/158 |
| 9,603,998 B2* | 3/2017 | Geipel et al. | A61M 5/16877 |
| 2002/0053242 A1 | 5/2002 | Tai et al. | |
| 2002/0097303 A1 | 7/2002 | Gulvin et al. | |
| 2002/0117517 A1 | 8/2002 | Unger et al. | |
| 2002/0127736 A1 | 9/2002 | Chou et al. | |
| 2003/0116738 A1 | 6/2003 | O'Connor et al. | |
| 2003/0200812 A1 | 10/2003 | Kuhn et al. | |
| 2004/0086427 A1 | 5/2004 | Childers et al. | |
| 2004/0209354 A1 | 10/2004 | Mathies et al. | |
| 2004/0222091 A1 | 11/2004 | Lauks et al. | |
| 2005/0230767 A1 | 10/2005 | Park et al. | |
| 2005/0279635 A1 | 12/2005 | Chow et al. | |
| 2006/0144151 A1 | 7/2006 | Krause et al. | |
| 2006/0213275 A1 | 9/2006 | Cobianu et al. | |
| 2007/0028683 A1 | 2/2007 | Ionescu-Zanetti | |
| 2007/0224084 A1 | 9/2007 | Holmes et al. | |
| 2007/0277623 A1 | 12/2007 | McDonald et al. | |
| 2009/0129952 A1 | 5/2009 | Patrascu et al. | |
| 2009/0288492 A1 | 11/2009 | Stewart et al. | |
| 2009/0317298 A1 | 12/2009 | McAvoy et al. | |
| 2010/0018584 A1 | 1/2010 | Bransky et al. | |
| 2010/0098585 A1 | 4/2010 | Chiu et al. | |
| 2010/0202038 A1 | 8/2010 | Chung et al. | |
| 2011/0137580 A1* | 6/2011 | Bartels et al. | G01F 1/34 |
| 2013/0127879 A1 | 5/2013 | Burns et al. | |
| 2013/0217598 A1 | 8/2013 | Ludwig et al. | |
| 2014/0273187 A1 | 9/2014 | Johnson et al. | |
| 2015/0048848 A1* | 2/2015 | Dawson et al. | G01N 27/221 |
| 2016/0033350 A1* | 2/2016 | Stokes et al. | G01L 19/14 |
| 2016/0052782 A1* | 2/2016 | Liu | B81C 1/00325 |
| 2017/0209643 A1* | 7/2017 | Geipel et al. | A61M 5/141 |

FOREIGN PATENT DOCUMENTS

| | | | |
|---|---|---|---|
| CN | 103185613 A | 7/2013 | |
| DK | 3367074 A1 * | 8/2018 | ............ G01L 19/06 |
| EP | 310225 A2 | 7/1988 | |
| FI | 883523 A | 2/1989 | |
| WO | 03000416 A2 | 1/2003 | |
| WO | 2008030284 A2 | 3/2008 | |
| WO | 09027897 A2 | 3/2009 | |
| WO | 2015114635 A1 | 8/2015 | |

OTHER PUBLICATIONS

Hasenkamp, et al., Polyimide/SU-8 catheter-tip MEMS gauge pressure sensor, Biomed Microdevices, 2012, pp. 819-828, vol. 14.

* cited by examiner

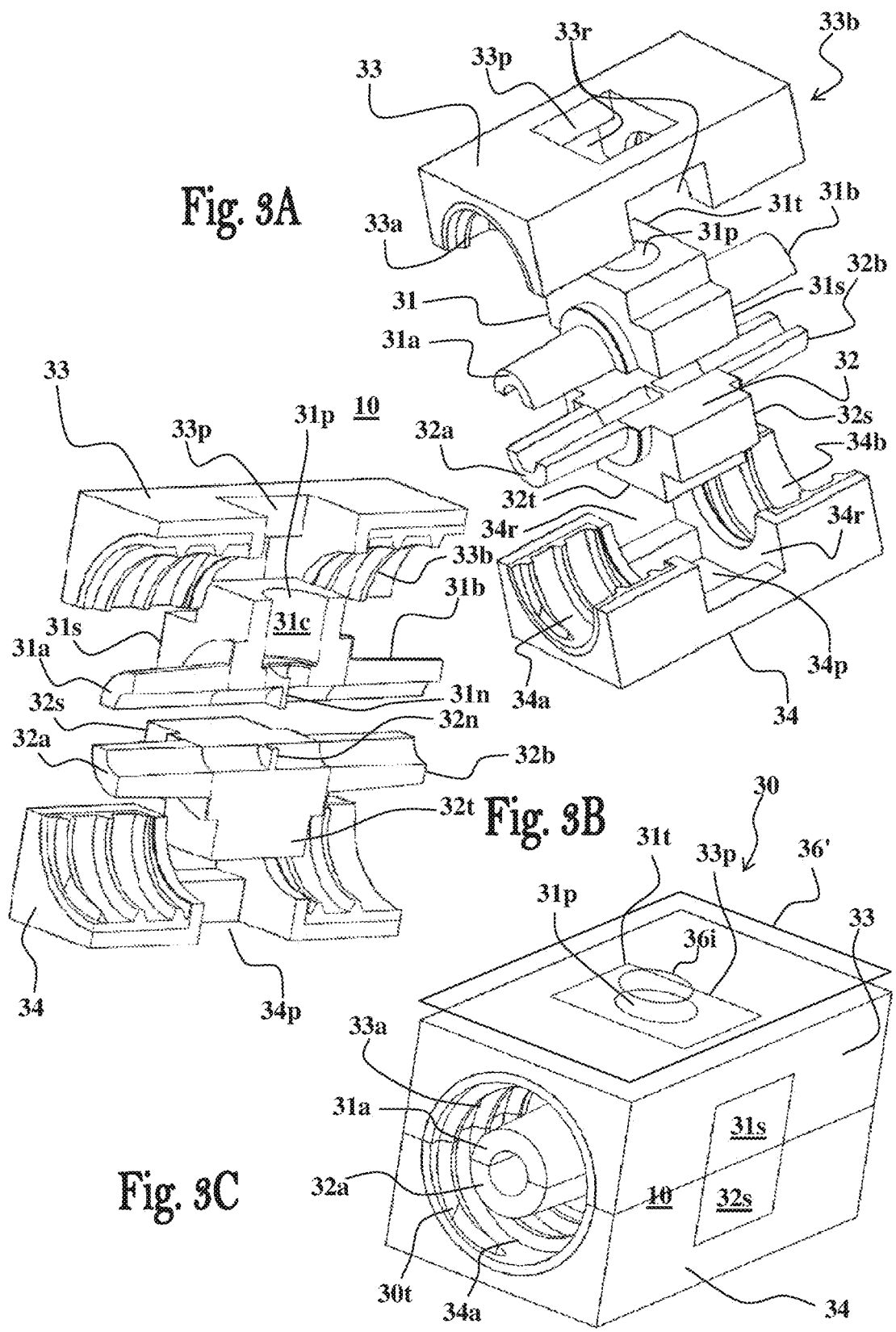

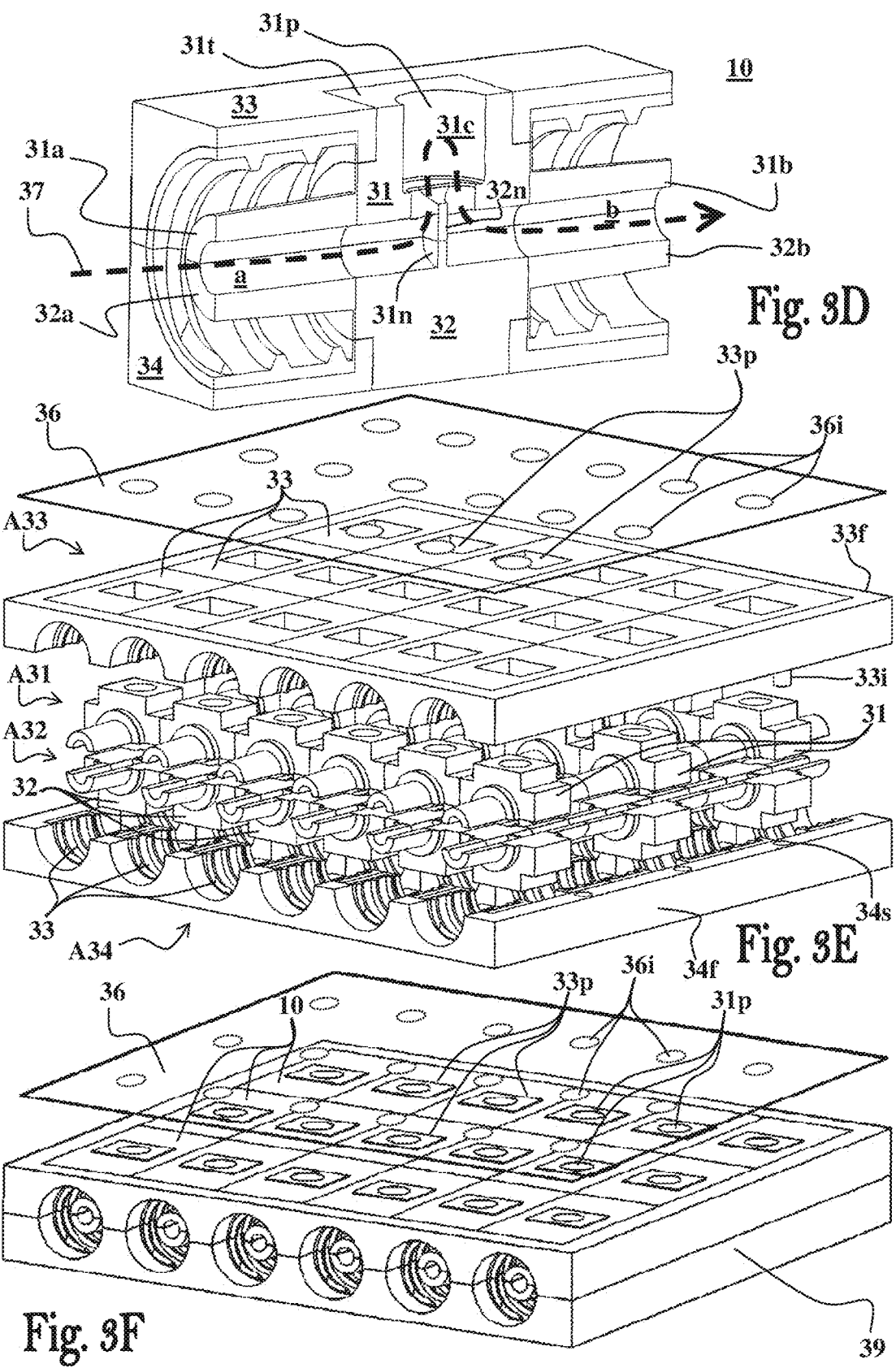

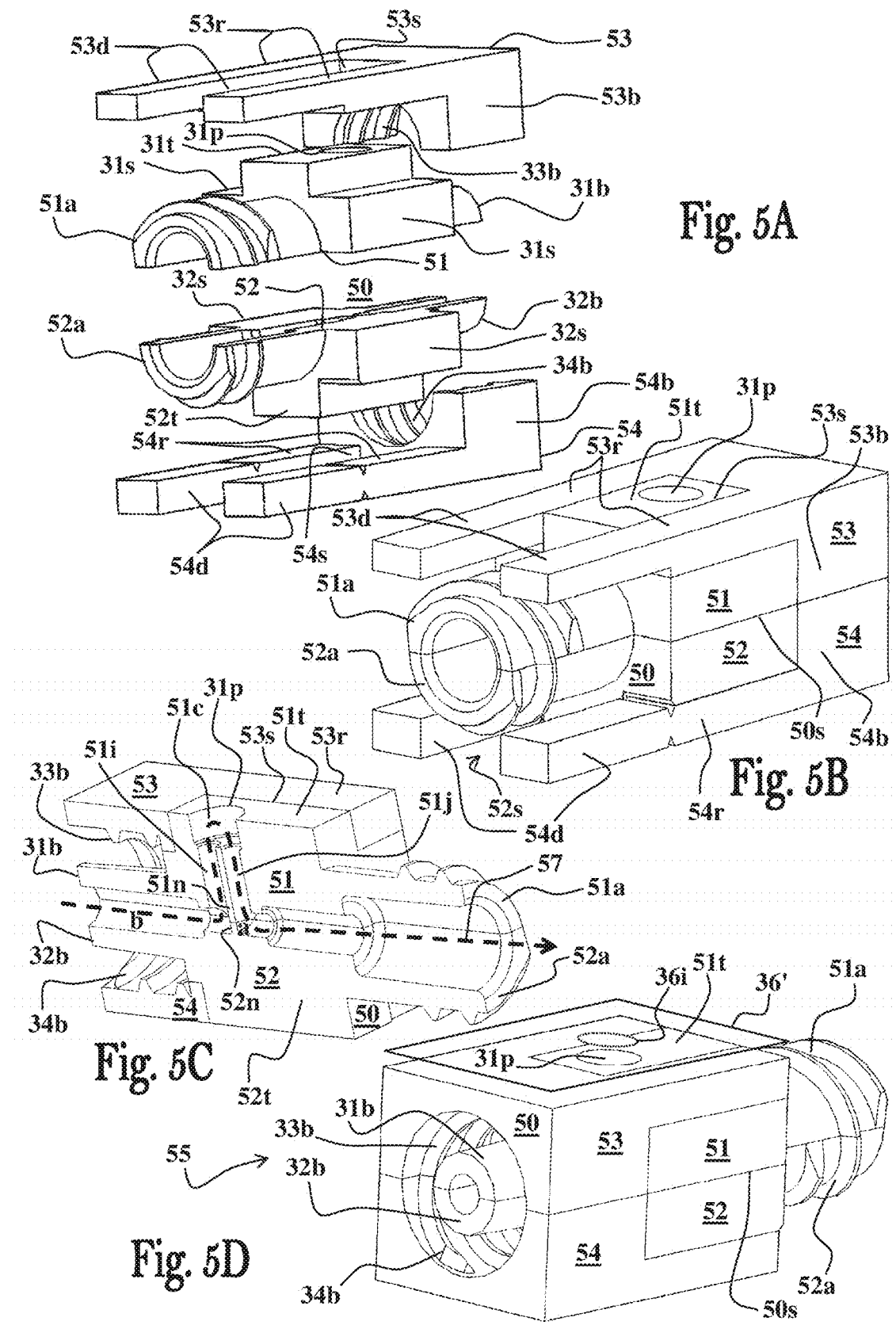

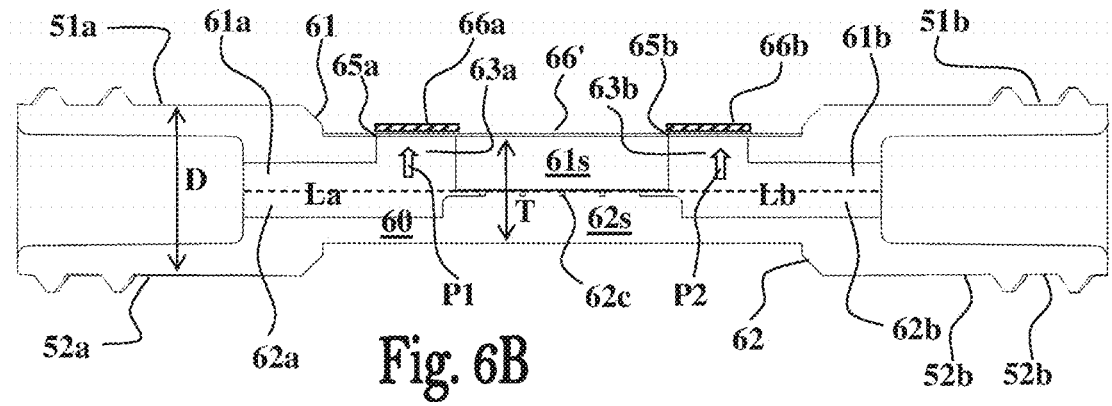
Fig. 6B
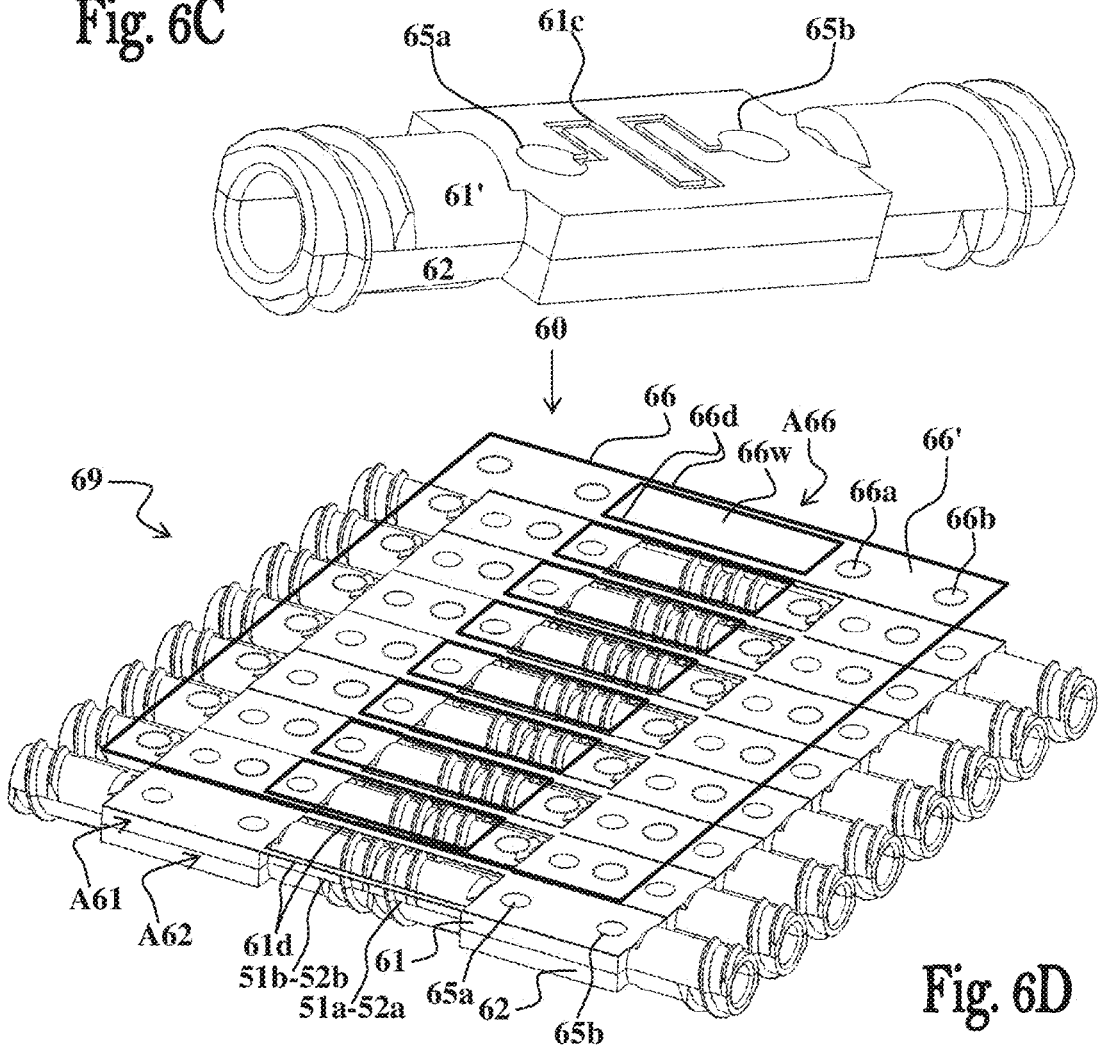
Fig. 6C
Fig. 6D

FLUIDIC MICROELECTROMECHANICAL SENSORS/DEVICES AND FABRICATION METHODS THEREOF

TECHNOLOGICAL FIELD

The present invention is generally in the field of fluidic microelectromechanical (MEM) sensor systems/devices.

BACKGROUND

MEM systems/devices (e.g., for medical usage) usually employ sensor elements implemented by semiconductor structures, where the fluid flow paths of these devices and their connections to external systems/devices, their packaging, and their mechanical/electrical interfaces are typically implemented by means of plastic elements. In addition, electrical connectivity of such MEM systems/devices with external systems is not implemented directly on the semiconductor die, and requires, inter alia, additional electrical interface involving wiring and electrical contacts, plastic structures, and printed circuit boards (PCB).

These manufacturing techniques require accurate and complex attachments of the semiconductor die to its carrier to achieve electrical and mechanical connectivity to guarantee that pressure forces are correctly transmitted to the sensing elements, and obtain proper alignment between the fluid flow structures formed in the plastic packaging with the sensors and/or actuators implemented in the semiconductor die. This combination of manufacturing techniques typically results in a costly, and considerably complex, fabrication and integration of the fluidic MEM sensor (e.g., Silicon) into the fluidic MEM.

Fluidic MEM devices fabrication techniques known from the patent literature are described in the following patent publications.

U.S. Pat. No. 7,311,693 describes a drug delivery device with a pressurized reservoir in communication with a flow path to an outlet. The flow path includes two normally-closed valves and a flow restriction. A pressure measurement arrangement measures a differential fluid pressure between two points along the flow path which span at least part of the flow restriction, one of the points being between the valves. A controller selectively opens the valves to deliver a defined quantity of the liquid medicament to the outlet.

U.S. Pat. No. 6,782,755 describes surface-micromachined high-pressure sensor, formed by forming a cavity using a sacrificial layer. The sacrificial layer can be reflowed to make the edges of the cavity more rounded. The material that is used for the diaphragm can be silicon nitride, or multiple layers including silicon nitride and other materials. The pressure sensor is intended to be used in high pressure applications, e.g. pressure is higher than 6000, 10,000 or 30,000 P.S.I.

US Patent Publication No. 2007/028683 describes a pressure sensing device and method for sensing pressure that utilizes a deformable cavity containing a conductive medium. Pressure changes induce deformations of the cavity, resulting in changes of conductivity, as measured by electrodes. The device may either sense pressure directly or may be used to sense the pressure in a separate cavity that is in close proximity Since the measurements do not require electrodes in the sensing region, the device is simple to fabricate. The device also has high sensitivity, making it suitable for microfluidic or biomedical applications where a low profile and disposable device is required.

GENERAL DESCRIPTION

Fabrication of the fluidic MEMSs used nowadays, for example, in medical devices, is a complex and expensive process requiring expertise, inter alia, in semiconductors fabrication technologies, plastic packaging techniques, and electronic circuit board design and manufacture. The sensor elements of the MEMSs are usually fabricated in semiconductor wafers, which are then diced, separately packaged, electrically/electronically equipped and wired. The packaged semiconductors then separately fluidly interfaced by adding fluid connectors/ports, and separately calibrated.

The present application provides MEMSs structures and fabrication techniques that significantly simplify the MEMSs production process, and substantially reduces the production costs and times. In a broad aspect the MEMSs disclosed herein are comprised of a main body structure having a fluid passage therealong and at least one opening in one of its walls in fluid communication with the fluid passage (i.e., the at least one opening opens into the fluid passage), and a sealing element attached on a surface area of the main body structure comprising the at least one opening to sealably close it and place thereover one or more electrical and/or sensor components patterned or attached thereon.

The one or more electrical and/or sensor components patterned/attached on the sealing element are configured to measure one or more properties and/or conditions of a fluid substance (such as a liquid and/or gaseous material) introduced into the fluid passage and interacting with the portion of the sealing element positioned over the at least one opening. In some embodiments the one or more electrical and/or sensor components are patterned/attached on the sealing element after it is attached to the main body structure.

The main body structure comprises in some embodiments at least one cavity along its fluid passage, the at least one cavity being in direct fluid communication with the at least one opening, and configured to receive thereinto fluid substance from the fluid passage and have it interact with the sealing element attached over the opening. The fluid passage can comprise at least one fluid restrictor/constriction and/or flow manipulating element associated with the cavity, for causing changes in the fluid flow rate and/or direction, and/or pressure therein.

Optionally, and in some embodiment preferably, the sealing element is made from a thin film or foil made of polymeric material (e.g., polyimide, polycarbonate, peek, ultem, polyurethane, etc.), and having thickness of about 10 to 1000 microns, and its one or more electrical and/or sensor components can be patterned by sputtering, evaporation, lamination, electroplating, electroless plating, electroforming, printing, and/or attached by means of printed circuit board surface mounting technology.

The one or more electrical and/or sensor components can be made from metals, semiconductor, polymers having specific electrical conductivity properties, piezoresistive materials, piezoelectric materials, or combinations thereof, according to the application and type sensing elements to be implemented (e.g., Gold, NiCr alloys, platinum, titanium). The thickness of the one or more electrical and/or sensor components can be between 50 angstrom to 50 microns, that can be applied using electrically conductive ink, by deposition, lamination, evaporation, sputtering, printing, electroless plating and/or electroplating, to assume any suitable shape (e.g., zig zag, serpentine, rosettes, etc).

The one or more electrical and/or sensor components can be configured to measure tension changes in portion of the sealing element on which they are patterned caused by deformation of the sealing element portion responsive to interaction with the fluid substance inside the fluid passage, for determining the one or more properties and/or conditions of the fluid substance (e.g., fluid pressure, flow rate, and suchlike).

Alternatively, or additionally, the one or more electrical and/or sensor components patterned on the sealing element can be configured to measure one more properties of the fluid induced through the sealing element (e.g., temperature). In some embodiments the one or more electrical and/or sensor components patterned on the sealing element are configured to physically contact the fluid substance inside the passage of the main body structure and thereby measure the one or more properties and/or conditions of the fluid substance (e.g., pH, reduction potential, electrical conductivity, and suchlike). Thus, in some embodiments, the sealing element comprises electrical and/or sensor components patterned/attached on both its upper and under sides, which can be electrically coupled by one or more vias.

Optionally, and in some embodiments preferably, the main body structure is assembled from two or more body elements having preformed channels and/or cavities, and configured to form the fluid passage by attaching the two or more elements one to the other, and/or the at least one cavity, and/or the at least one fluid restrictor/constriction and/or flow manipulating element. At least some of the two or more body elements can comprise structural patterns configured to form fluid ports and/or connectors in fluid communication with the fluid passage of the main body structure. The two or more body elements can be configured to be assembled in a layer by layer form, so as to form a multilayered structure comprising the different elements of the main body structure i.e., the fluid passage, and the at least one cavity and/or the at least one fluid restrictor/constriction and/or the at least one flow manipulating element and/or the fluid ports/connectors.

The layered assemble approach of the main body structures of the MEMSs is utilized in some embodiment for fabrication of a layered wafer comprising an array of main body structures of the MEMSs. Particularly, each of the two or more body elements can be fabricated in an array of integrally formed such body elements, and the layers of integrally comprised body elements can be attached one to the other to form the array of main body structures the MEMSs.

A sealing sheet comprising a respective array of the sealing elements, each having its at least one electrical and/or senor components patterned/attached thereon, is then attached over the wafer such that each one of its sealing elements is attached on a respective main body structure to sealably close the at least one opening of the main body structure and accurately locate the at least one electrical and/or senor component over its respective opening. This way a wafer comprising an array of MEMSs is constructed in a layered fashion that can be advantageously used to calibrate all of MEMSs in a single calibration step, as described herein in U.S. Provisional Patent application No. 62/470,407, of the same applicant hereof, the disclosure of which is incorporated herein by reference.

Advantageously, each one of the different body elements of the MEMS is configured such that it can be easily fabricated by any conventional 3D object production technique without presenting undercuts and/or need to form partially or fully closed cavities. With this design the layers comprising the arrays of the body elements can be similarly fabricated by any conventional 3D object production technique without presenting undercuts and/or need to form partially or fully closed cavities.

Optionally, and in some embodiments preferably, the electrical and/or sensor components are patterned/attached on the sealing element/sheet before it is attached to the main body structure/wafer comprising the array of main body structures. In some embodiments the electrical and/or sensor components are patterned/attached on the sealing element/sheet after it is attached to the main body structure/wafer comprising the array of main body structures.

The wafer of MEMSs can be diced, before or after the calibration of the MEMSs, using any suitable wafer dicing technique to cut out each of the MEMSs therefrom.

One inventive aspect of the subject matter disclosed herein relates to a fluidic sensor device comprising a base body structure comprising a fluid channel passing along the base body structure and at least one opening in an external face of the base body structure and being in fluid communication with the fluid channel, and a sealing element comprising one or more sensing elements a priori patterned or mounted thereon, the sealing element sealably attached over the external face of the base body structure comprising the at least one opening such that its one or more sensing elements become located over the at least one opening. The one or more sensing elements configured to measure at least one property or condition of a fluid substance when the fluid substance is introduced into the fluid channel and interact with a portion of the sealing element located over the at least one opening. Optionally, the base body structure comprises at least one open cavity in fluid communication with the fluid channel.

Optionally, and in some embodiments preferably, the base body structure is assembled from two or more separate body elements configured to attach one to the other and thereby form the fluid channel passing along the base body structure. At least one of the two or more separate body structures can comprise the at least one opening configured to form the at least one opening in the external face of the base body structure and being in fluid communication with the fluid channel when the two or more separate body elements are attached one to the other to assemble the base body structure.

The base body structure can comprise at least one fluid port adapted to connect to a fluid source. The at least one fluid port can be assembled by the attachment of the two one or more body elements, and being in fluid communication with the fluid channel.

Optionally, and in some embodiments preferably, the fluid channel comprises at least one fluid restrictor. The at least one fluid restrictor can be assembled from at least two restrictor portions elements by the attachment of the two or more body elements.

In some embodiments the at least two body elements comprise two channel forming body elements, each of the two channel forming body elements comprises a base portion and at least one open channel extending along a length of the base portion. The at least one open channel of the two body elements can be configured to form at least a portion of the fluid channel being in fluid communication with the at least one opening when attached one to the other. Optionally, and in some embodiments preferably, each of the two channel forming body elements comprises a respective at least one connector portion extending from its base portion and configured to form a connector structure when the two channel forming body elements are attached one to the other. Each of the two channel forming body elements can comprise a respective at least one partition portion configured to form a partition inside the fluid channel when the two channels forming the body elements are attached one to the other. Optionally, the at least two body elements comprise two casing body elements configured to attach one to the other and thereby form an enclosure fixedly encasing all other body elements therein.

In some embodiments the base portion of one of the two channels forming the body elements comprises first and second cavities with respective first and second openings formed in a wall thereof, where each opening opens into its respective cavity and sealably covered by a portion of the sealing element comprising a respective sensing element. The base portion of the other one of the two channel forming body elements can comprise a slender channel having first and second ends configured to respectively fluidly communicate with the first and second cavities when the body element are attached one to the other. Alternatively, the base portion of one of the two channel forming body elements comprises first and second cavities with respective first and second openings formed in a wall thereof, each opening opens into its respective cavity and sealably covered by a portion of the sealing element comprising a respective sensing element, and a slender channel having first and second ends configured to respectively fluidly communicate with the first and second cavities, where the slender channel is sealably closed by the sealing element.

The sealing element can comprise a pass through bore configured to be located over the first opening and fluidly communicate therewith to thereby form a fluid transmission passage, and the second opening can be sealably covered by a portion of the sealing element comprising the at least one sensing element. A flow transmission body element comprising an elongated open channel can be used to sealably attach over a portion of the sealing element and fluidly communicate between the fluid transmission passage and the portion of the sealing element sealably covering the second opening.

Optionally, and in some embodiments preferably, at least a portion of the sealing element is a multilayered element, such as a laminated layered structure, having at least one sealing layer configured to attach to the base body structure and seal the at least one opening, and at least one sensing layer located above said at least one sealing layer and comprising the one or more sensing elements. In some embodiments the multilayered sealing element comprises an inner layer comprising the sensing element sealably sandwiched between two protective layers. Optionally, at least one of the layers of the sealing element configured to allow bonding (e.g., by laser, ultrasonic, gluing) to the base body structure. The two protective layers are made in some embodiments from one or more biocompatible materials.

The sealing element can be a multilayered element constructed as described and illustrated in U.S. Provisional application No. 62/523,315, and/or in U.S. Provisional application No. 62/423,219, both of the same applicant hereof, the disclosures of which is incorporated herein by reference. Optionally, and in some embodiments preferably, the sealing element in the various embodiments disclosed herein comprises additional circuitries and electronic element configured to communicate measurement and/or control data with external machinery/systems, as described and illustrated in U.S. Provisional application No. 62/470,407, of the same applicant hereof, the disclosure of which is incorporated herein by reference.

Optionally, the one or more sensing elements are patterned or mounted on the sealing element after it is attached to the base body structure Optionally, the flow transmission body element comprises an opening formed in a wall thereof covered by a gas discharge component, where the gas discharge component configured to eject gasses trapped inside the elongated channel of the flow reversing body element.

Optionally, and in some embodiments preferably, at least a portion of the sealing element attached over the at least one opening is deformable, and the one or more sensing elements are configured to measure the at least one property or condition of the fluid responsive to deformations of the portion of the sealing element. The one or more sensing elements can comprise a temperature sensor being configured for measurement of temperature of the fluid substance contacting the sealing element. The one or more sensing elements can comprise at least one electrode positioned on an underside of the sealing element and configured to become in physical contact with the fluid substance when streamed through the fluid channel. Accordingly, the sealing element comprises in some embodiments at least one via for electrically coupling to the at least one electrode by means of contacts pads on the upper side of the sealing element.

The base body structure comprises in some embodiments a shielding element attached over a portion of the sealing element comprising the at least one sensing element and configured to prevent deformations of the portion of the sealing element. The shielding element can be configured to thermally isolate the portion of the sealing element from external environment and to prevent at least one of physical user contact with the at least one sensing element and detachment of the sealing element.

In some embodiments the base body structure comprises a shielding element attached over a portion of the sealing element comprising the at least one sensing element, where the shielding element comprises an open cavity configured to be placed over a portion of the sealing element covering one of the at least one opening and thereby enable deformation of the portion of the sealing element while thermally and/or physically isolating it from the external environment. Optionally, the open cavity comprises one or more openings configured to allow entry of air from the external environment into the cavity. Alternatively, the open cavity can be configured to maintain a predetermined pressure level over a portion of the sealing elements covering one of the at least one opening. The shielding element can comprise one or more fastening pins configured to fasten the shielding element to the base body structure.

Optionally, and in some embodiments preferably, the body elements of the base body structure are fabricated by three-dimensional object production techniques without presenting undercuts or closed cavities.

Another inventive aspect of the subject matter disclosed herein relates to a wafer comprising an array of fluidic sensor devices according to any one of the embodiments described hereinabove and hereinbelow integrally assembled therein by attaching two or more layers one to the other. The wafer comprises in some embodiments a sealing sheet comprising a respective array of the sealing elements sealably attached to a respective array of base body structures for covering their openings and placing the a priori patterned or mounted sensing elements thereover.

In some embodiments the array of base body structures is assembled from two or more arrays of body elements configured to form elements of said fluidic sensor devices when attached one to the other.

Each of the layers can comprise an array of one of the body elements configured to form elements of the fluidic sensor devices when attached to at least one other layer. A sealing sheet comprising a respective array of the sealing elements is sealably attached to one of the layers for covering the opening of its body element and placing the sensing elements thereover. Optionally, each body element in at least one of the layers comprises at least one support element configured to connect the body element to at least one other adjacent body element in the layer.

Yet another inventive aspect of the subject matter disclosed herein relates to a wafer for construction of an array of fluidic sensor devices according to any one of the embodiments disclosed hereinabove and hereinbelow, the wafer comprising a holder assembly comprising a plurality of sockets each configured to snugly receive a base body structure of one of the fluidic sensor devices and firmly hold it therein to thereby facilitate placement of a sealing sheet comprising a respective array of the sealing elements thereover. The wafer can comprise a support frame having a respective plurality of sockets each configured to snugly attach over one of the base body structures of fluidic sensor devices in the holder and firmly hold it in place, where the support frame comprising one or more elongated windows configured to facilitate attachment of sealing sheets comprising the sealing elements over one or more rows of said base body structures.

Optionally, the holder arrangement and it support frame are configured to sealably communicate between two or more adjacently located fluidic sensor devices. The support frame can comprise one or more connectors, each sealably connected to the two or more adjacently located fluidic sensor devices sealably communicated by the holder arrangement and it support to enable concurrently calibrating them in a same calibration process.

A yet further inventive aspect of the subject matter disclosed herein relates to a method of constructing fluidic sensor device by forming a base body structure having a fluid channel passing along the base body structure and being in fluid communication with at least one opening in an external face of the base body structure, and attaching a sealing element comprising one or more sensing elements a priori patterned or mounted thereon over the external face of the base body structure comprising the at least one opening such that its one or more sensing elements become located over the at least one opening. In some embodiments the base body structure is constructed by attaching two or more separate body elements to thereby form the fluid channel in fluid communication with the at least one opening.

The one or more sensing elements can be configured to measure at least one property or condition of a fluid substance when the fluid substance is introduced into the fluid channel and interact with a portion of the sealing element located over the at least one opening. Optionally, the assembling comprises forming at least one fluid port by the attachment of the two one or more body elements, and the at least one fluid port being in fluid communication with the fluid channel. The assembling can also comprise forming at least one fluid restrictor in the fluid channel by the attachment of the two or more body elements. Optionally, the assembling comprises attaching two casing body elements one to the other to form an enclosure fixedly encasing all other body elements therein.

A yet additional inventive aspect of the subject matter disclosed herein relates to a method of constructing a wafer integrally comprising an array of the fluidic sensor device according to any one of the embodiments described hereinabove and hereinbelow. The method can comprise preparing an array of body base structures, patterning or mounting on a sealing sheet an array of one or more sensing elements, and attaching the sealing sheet over said array of the base body structures so as to seal the respective at least one openings of the base body structures and place respective one or more sensing elements thereover.

In some possible embodiments the wafer is constructed by preparing a plurality of layers, each layer comprising an array of one the body elements, attaching the plurality of layers one to the other to form a respective array of the base body structures, preparing a sealing sheet comprising a respective array of the sealing elements, patterning or mounting in each sealing element one or more sensing elements, and attaching the sealing sheet over the array of the base body structures to thereby seal the respective at least one openings of the base body structures and place respective one or more sensing elements thereover.

BRIEF DESCRIPTION OF THE DRAWINGS

In order to understand the invention and to see how it may be carried out in practice, embodiments will now be described, by way of non-limiting example only, with reference to the accompanying drawings. Features shown in the drawings are meant to be illustrative of only some embodiments of the invention, unless otherwise implicitly indicated. In the drawings like reference numerals are used to indicate corresponding parts, and in which:

FIGS. 1A and 1B schematically illustrate fluidic MEMS according to some possible embodiments comprised of a fluid flow structure and a sealing membrane/deformable element attached thereto and comprising sensing and electrical structures thereon, wherein FIG. 1A shows a sectional view of the fluidic MEMS and FIG. 1B shows fabrication of a plurality of the fluidic MEMS in a wafer;

FIG. 2C shows attachment of a sealing deformable element/membrane to the layered fluid flow structure;

FIG. 3A to 3F schematically illustrate fluidic MEMS of some possible embodiments comprising a multilayered fluid flow structure, wherein FIG. 3A shows an exploded perspective view of the multilayered fluid flow structure, FIG. 3B shows a sectional exploded perspective view of the multilayered fluid flow structure, FIG. 3C shows a perspective view of the multilayered fluid flow structure; FIG. 3D shows a sectional perspective view of the multilayered fluid flow structure; and FIGS. 3E and 3F show construction of a wafer comprising an array of MEMSs with multilayered fluid flow structures and a sealing membrane/deformable element;

FIGS. 4A and 4B schematically illustrate fluidic MEMS of some possible embodiments configured for temperature measurements, wherein FIG. 4A shows a perspective view of the MEMS and FIG. 4B shows construction of a wafer comprising an array of the MEMSs;

FIGS. 5A to 5H schematically illustrate fluidic MEMS of some possible embodiments comprising male and female connector elements, wherein FIG. 5A shows an exploded perspective view of a preassembled fluid flow structure of the MEMS, FIG. 5B shows a perspective view of the assembled fluid flow structure of the MEMS before dicing, FIGS. 5C and 5D respectively show sectional and back perspective views of the fluid flow structure of the MEMS after dicing, FIG. 5E shows construction of a wafer comprising an array of the fluidic MEMSs, FIGS. 5F and 5G show a possible process for dicing the array of the fluidic MEMSs, and FIG. 5H shows construction of a wafer comprising an array of the fluidic MEMSs using a plurality of separate sealing sheets/foils;

FIGS. 6A to 6F schematically illustrate fluidic MEMS of some possible embodiments comprising two female connector elements, wherein FIGS. 6A and 6B respectively show a perspective-exploded view and a side-sectional view of the fluidic MEMS, FIG. 6C shows a variant of the fluidic MEMS comprising an upper slender channel, FIG. 6D shows construction of a wafer comprising an array of the fluidic MEMSs, FIG. 6E shows a possible process for dicing the array of fluidic MEMSs, and FIG. 6F shows construction of an array of the fluidic MEMSs using separate sealing sheets/foils;

FIG. 7C shows a sectional view of the fluid MEMS, FIG. 7D shows a sectional view of the sealing element, and FIG. 7E shows construction of a wafer comprising an array of the fluidic MEMSs and a possible process for dicing the same;

FIGS. 8A to 8E schematically illustrate fluidic MEMS of some possible embodiments comprising a conductivity sensing element, wherein FIG. 8A shows an exploded perspective view of the preassembled fluidic MEMS, FIG. 8B shows a perspective sectional view of the fluidic MEMS, FIG. 8C shows a perspective view of a sealing element of the fluidic MEMS with sensing and electrical elements patterned on its top and bottom sides, and FIGS. 8D and 8E show construction of a wafer comprising an array of the fluidic MEMS;

FIGS. 9A to 9E schematically illustrate fluidic MEMSs of some possible embodiments comprising several sensing elements, wherein FIG. 9A shows an exploded perspective view of a preassembled fluidic MEMS, FIG. 9B shows a perspective sectional view of the MEMS, FIGS. 9C and 9D show exploded perspective views of modifications of the MEMS, and FIG. 9E illustrates possible attachment of a shielding element to the body of the MEMSs;

FIGS. 10A to 10C schematically illustrate arrangements configured for holding an array of fluidic MEMSs, wherein FIG. 10A shows a perspective view of an arrangement for holding a single row of MEMSs, and FIGS. 10B and 10C show perspective views of arrangements for holding an array of MEMSs; and FIGS. 11A to 11C schematically illustrate fluidic MEMS of some possible embodiments implemented without fluidic channel(s), wherein FIG. 11A shows an application of the fluidic MEMS for a sealing element, FIG. 11B shows fabrication of an array of the fluidic MEMSs; and FIG. 11C demonstrates applications of the fluidic MEMSs in a syringe hub and/or barrel.

DETAILED DESCRIPTION OF EMBODIMENTS

Figure 1A:
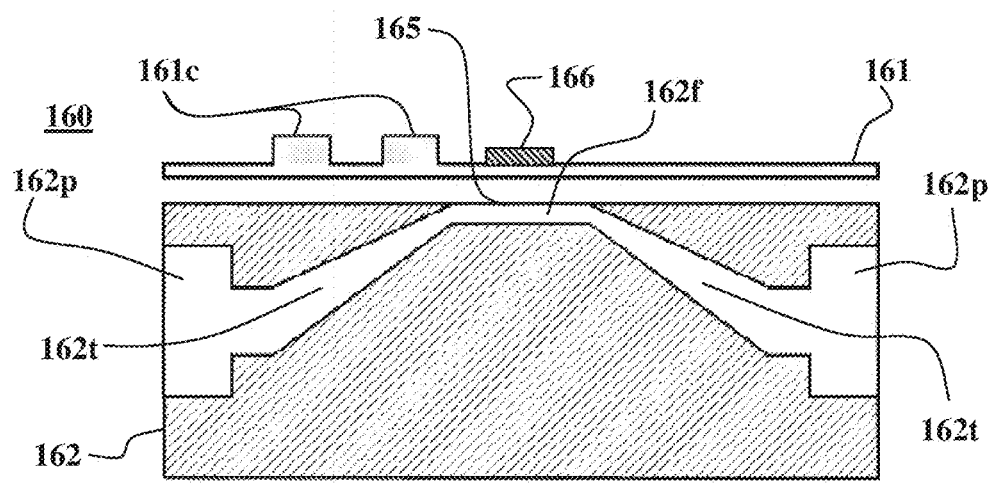

One or more specific embodiments of the present disclosure will be described below with reference to the drawings, which are to be considered in all aspects as illustrative only and not restrictive in any manner. In an effort to provide a concise description of these embodiments, not all features of an actual implementation are described in the specification. Elements illustrated in the drawings are not necessarily to scale, or in correct proportional relationships, which are not critical. Emphasis instead being placed upon clearly illustrating the principles of the invention such that persons skilled in the art will be able to make and use the fluidic MEMS, once they understand the principles of the subject matter disclosed herein. This invention may be provided in other specific forms and embodiments without departing from the essential characteristics described herein.

The present application provides structures, and fabrication techniques, for MEMSs comprised of several layers, each of which can be separately manufactured from same or different material. In some embodiments the MEMSs comprise a main body structure made of two or more body parts separately prepared using any suitable three-dimensional (3D) object production techniques, and configured to attach one to the other is layer by layer fashion. In some embodiments at least some of the body parts of the MEMSs are manufactured by injection molding, computer numerical control (CNC) milling, 3D printing. Optionally, and in some embodiments preferably, at least one, or all, of the body parts of the MEMSs are manufactured from plastic/polymeric materials using the above-mentioned production techniques, or any other suitable plastic manufacturing technique.

A thin sealing element (e.g., foil or film) comprising one or more sensor/electrical elements is attached to the main body structure to seal at least one opening formed therein and accurately place the one or more sensor/electrical elements over the one or more openings. The one or more sensor/electrical elements can be patterned on the sealing element (e.g., by metal deposition/lamination and then lithography). The sealing element can be manufactured by spinning, roll to roll, or any other suitable technique.

The fluidic MEMSs of the present application can be advantageously manufactured in form of arrays of MEMSs assembled by attaching two or more different and separately fabricated layers to form a wafer comprising a plurality of the fluidic MEMSs. The fluidic MEMSs are then cut/diced our from the wafer using any suitable wafer cutting/dicing technique, such as, but not limited to, laser cutting, mechanical sawing, water jet cutter, and hot wire cutting. Optionally, and in some embodiments preferably, the different layers of the MEMSs array are manufactured form polymeric materials, which are then assembled to form a polymeric wafer comprising an array of the fluidic MEMSs.

The multilayered MEMSs (plastic/polymeric) wafer construction techniques described herein can advantageously overcome the manufacturing limitation commonly encountered in plastic fabrication techniques. For example:
  injection molding manufacture techniques cannot be used to manufacture undercuts (recessed surfaces) or empty closed volumes in a single mold;
  in many cases 3D printing cannot be used to create undercuts without a support;
  3D printing techniques also cannot be used to manufacture objects with empty closed volumes, as these techniques requires that a drainage opening be formed to empty the cavity from the uncured material(s).

The multilayered MEMSs fabrication techniques disclosed herein can be used to manufacture arrays of MEMSs having different structures and forms from the examples provided herein, without departing from the scope and spirit of the present application. For example, the MEMSs structures described in international patent publication No. WO 2015/114635, of the same applicant hereof, the disclosure of which is incorporated herein by reference, can be fabricated as multilayered structures/wafers using any of the techniques described herein.

FIG. 1A schematically illustrate a fluidic MEMS/device 160 comprising, according to some possible embodiments, a fluid flow base element/structure 162 having at least one fluid port 162$p$ and at least one cavity or fluid flow path 162$f$ in fluid communication with the at least one fluid port 162$p$ via at least one fluid passage 162$t$, and at least one elastically deformable layer 161 (e.g., thin membrane/film/foil, also referred to herein as encapsulating/sealing layer) attached thereto. The base element 162 is structured and arranged with an opening 165 provided in one of its surface areas, said opening 165 being in fluid communication with the at least one cavity or fluid flow path 162$f$ and is sealably closed by the deformable layer 161 attached thereover.

In the specific non-limiting example shown in FIG. 1A, the fluid flow base element/structure 162 is a unitary element (monolithic i.e., made from one piece material), the at least one cavity or fluid flow path 162$f$ is formed along a section of the top side surface of the base element 162, and it is in fluid communication with two lateral fluid ports 162$p$ via respective two fluid passages 162$t$ having lumens that taper upwardly towards the at least one cavity or fluid flow path 162$f$. However, lumens of the fluid passages 162$t$ are not essentially having tapering configurations, and indeed in some embodiments the lumens in the MEMS/device are not tapering, or only slightly/partly tapper.

The numeral 166 in FIG. 1A references electrical conducting lines, sensing elements (e.g., for sensing fluid pressure inside the at least one cavity or fluid flow path 162$f$), electric circuitries, and/or actuating means for regulating fluid flow through the at least one cavity or fluid flow path 162$f$, pattered and/or mounted on a surface area of the deformable layer 161 located above the at least one cavity or fluid flow path 162$f$, using any suitable technique e.g., sputtering, evaporation, lamination, electroplating, electroless plating, electroforming, printing, and/or printed circuit board surface mounting technology. Electrical contacts/pads 161$c$ can be also patterned on the deformable layer 161, preferably, but not essentially, on a surface area not affected by its deformations. Accordingly, the MEMS/device 160 is generally constructed from the two main layers, the base element 160 with its fluid flow structures, and the deformable layer 161 attached thereover sealing the top opening 165 of the at least one cavity or fluid flow path 162$f$.

In some embodiments, the base element 162 and the deformable layer 161 are made from a same (or different) type of polymeric material, or any other suitable material (e.g., by lamination, CNC or micro-CNC, 3D printing, micro scale molding, micro machining, nano and micro imprinting, hot embossing, injection molding, lithography, laser micromachining, additive manufacturing, and suchlike).

Figure 1B:
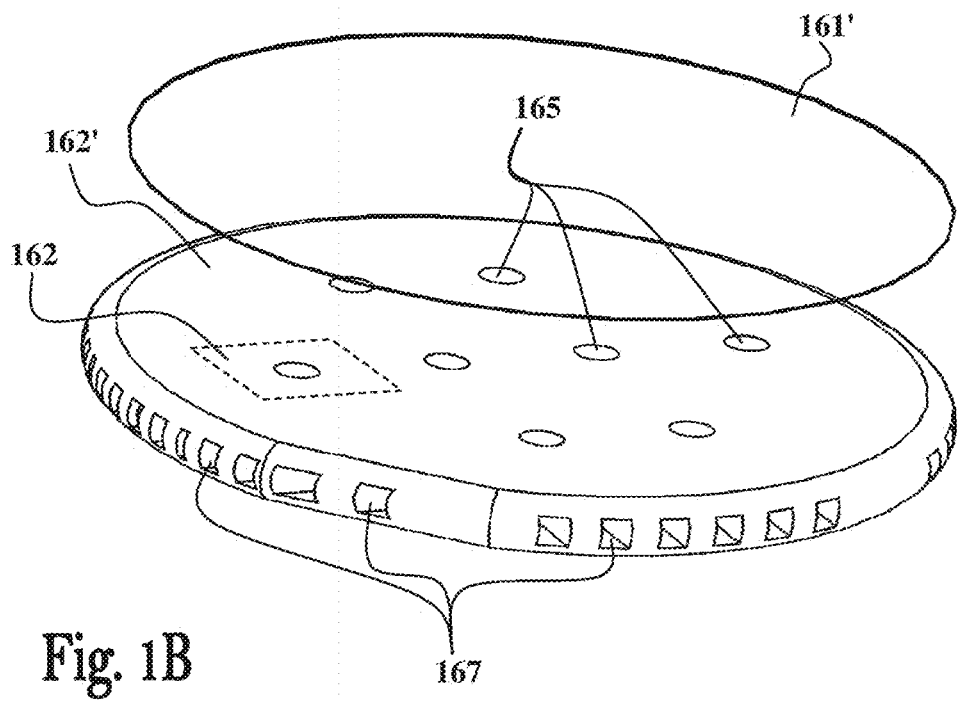

FIG. 1B demonstrates fabrication of a plurality of the fluidic MEMSs/devices 160 according to some possible embodiments. The base elements 162 of the MEMSs/devices 160 are fabricated in this non-limiting example as dies in the wafer 162' (also referred to herein as MEMSs production wafer) structured and arranged to form the inner fluid flow structures (not shown) of each MEMS/device 160, being in fluid communication with a respective top opening 165 thereof. A common elastically deformable layer 161' is attached (e.g., by lamination, ultrasonic welding, bonding, gluing, laser welding) on top of the wafer 161' for sealably closing the top openings 165 of all of the base elements 162 in the wafer 161'. After attaching the deformable layer 161' over the top surface and closing the openings 165, the plurality of MEMSs/devices 160 are cut (diced, illustrated by a dashed-line rectangle) out from the obtained layered structure using any known suitable dicing technique.

The electrical contacts/pads (161$c$ in FIG. 1A), and/or the electrical conducting lines and/or circuitries, and/or the sensing elements, and/or the actuating means (166 in FIG. 1B) can be formed or mounted on the deformable layer before or after cutting out the MEMSs/devices 160, using any of the techniques described hereinabove. Optionally, additional circuitries (e.g., a controller, data communication means, memories, passive components, such as, but not limited to, resistors, capacitors and inductors) are patterned/deposited/mounted on the MEMSs/devices 160 for handling electrical signals thereby and externally received control signals, and/or for communicating (via the electrical contacts/pads, or wirelessly) these signals with one or more external devices. In some possible embodiments the actuating means placed on the deformable layer are configured to regulate the fluid flow through the at least one cavity or fluid flow path 162$f$ responsive to mechanical or electromagnetic external control e.g., applied by an external device.

The wafer 162' comprises a plurality of lateral openings 167, at least some of which are in fluid communication with its internal fluid flow structures. As seen, in this specific and non-limiting example, the lateral openings 167 are of rectangular geometrical shape to allow sealing them easily (e.g., using glue, adhesive tape, sealably fitting plugs, and suchlike) to prevent contamination of the inner fluid passages, cavities/flow paths. In possible embodiments the wafer 162' does not include the lateral openings 167.

Figure 2A:
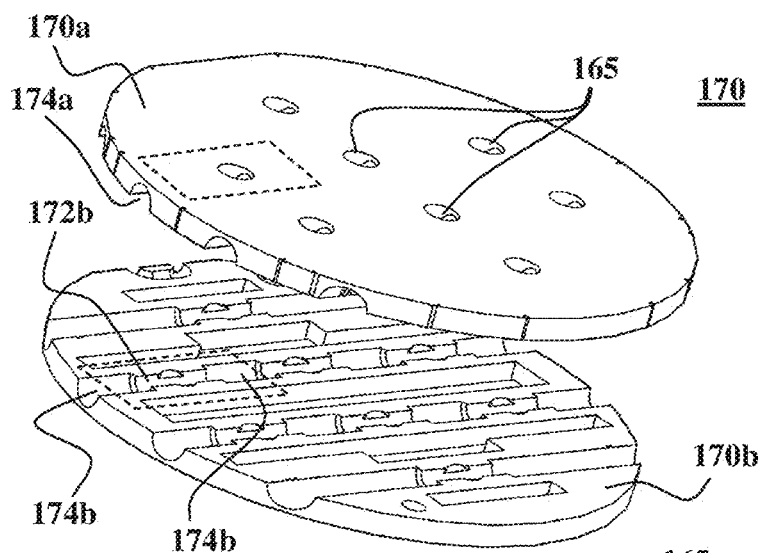
FIGS. 2A to 2C schematically illustrate fluidic MEMSs array comprising in some possible embodiments a layered fluid flow structure, wherein FIGS. 2A and 2B respectively show top and bottom perspective views of the fluid flow structure.
Figure 2B:
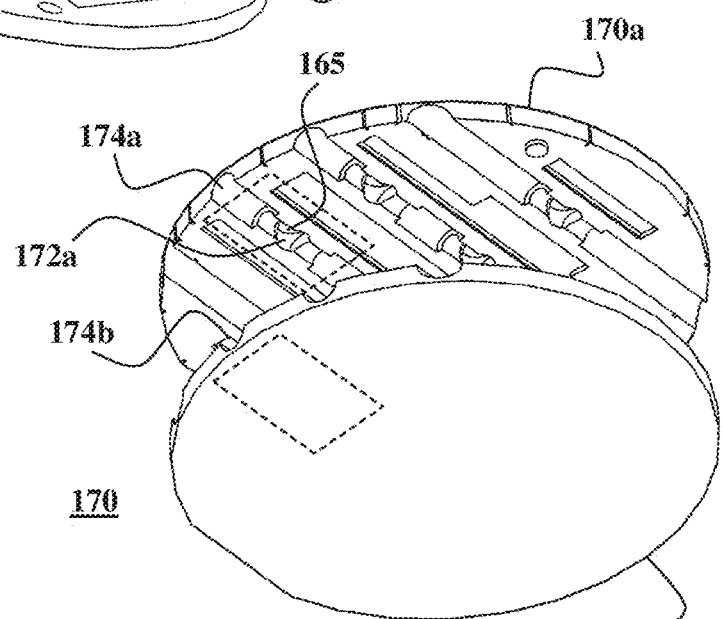
Figure 2C:
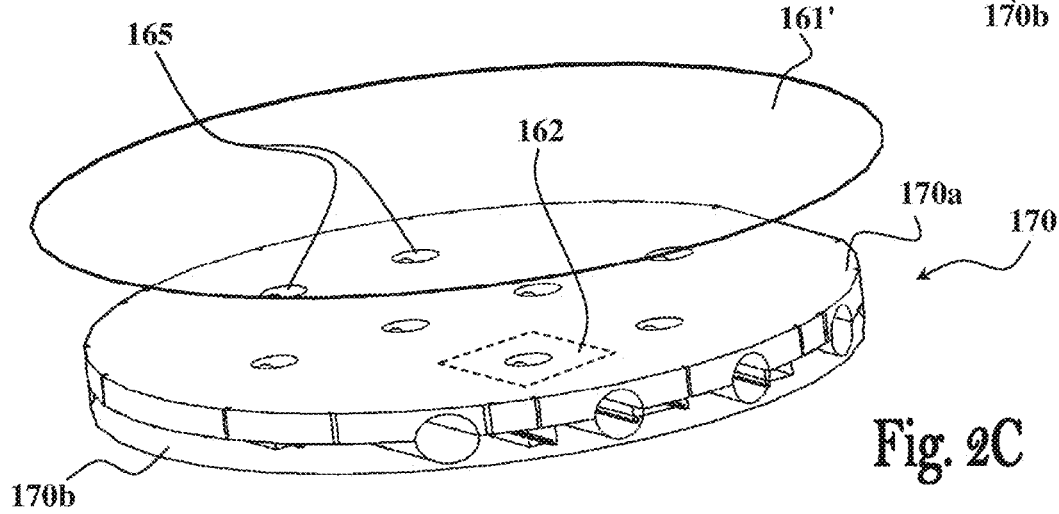

FIGS. 2A to 2C schematically illustrate another possible technique of fabricating a plurality of the fluidic MEMSs/devices 160 shown in FIG. 1A. As seen in FIGS. 2A and 2B, in this non-limiting example the wafer 170 (also referred to herein as MEMSs production wafer) is assembled from two different and separately fabricated layers configured to form the fluid flow structures of the base elements (162) by sealably attaching one layer to the other. The bottom layer 170$b$ of the wafer 170 is structured and arranged with a fluid port portions 174$b$ and cavity/fluid flow channel portions 172$b$, and the top layer 170$a$ of the wafer 170 is structured and arranged with complementary fluid port portions 174$a$ and cavity/fluid flow channel portions 172$a$, and respective openings 165 in fluid communication with their respective fluid port portions 174$a$.

The top layer 170$a$ can be attached to the bottom layer 170$b$ of the wafer 170 by lamination, ultrasonic welding, bonding, gluing, or laser welding. The attachment of the layers 170$a$ and 170$b$ in alignment of their fluid interaction portions sealably construct the fluid ports, fluid passages, and cavities/fluid flow paths/lumens of the base elements. For example, and without being limiting, if laser welding is used, the top layer 170$a$ can be a thermoplastic laser adsorbent layer, the bottom layer 170$b$ can be a thermoplastic transparent laser layer, and the deformable layer 161' can be a laser transparent layer.

FIG. 2C shows attachment of a common elastically deformable layer 161' on top of the top layer 170$a$ of the assembled wafer 170, sealing the openings 165 of the base elements 162 integrated in it. The deformable layer 161' can be attached on the top layer 170$a$ to sealably close its openings 165, using any of the techniques described herein, or any other suitable technique. After attaching the deformable layer 161' over the top surface and closing the openings 165, the plurality of MEMSs/devices 160 are cut (diced, illustrated by a dashed-line rectangle) out from the obtained layered structure using any known suitable dicing technique.

In some possible embodiments the top layer 170*a* is structured and arranged to integrally include deformable elements i.e., by fabricating the top layer 170*a* to include elastic/flexible thin regions instead of the opening 165. In this configuration attachment of the common deformable layer 161' on top of the top layer 170*a* is only optional and it can be omitted.

The top and/or bottom layers 170*a* and 170*b*, and/or the deformable layer 161', can be manufactured from polymeric materials (same or different) by any suitable technique, such as described herein. The electrical contacts/pads, and/or the electrical conducting lines, and/or the sensing elements, and/or the actuating means, and/or any additional circuitries (e.g., a controller, data communication means), can be patterned/mounted on the deformable layer 161' before or after cutting out the MEMS device 160, using any of the techniques described herein, or any other suitable technique.

FIGS. 2A to 2C demonstrate aligning the portions of the fluid interacting structures in the layers 170*a* and 170*b* in parallel structures, but of course any other suitable arrangement can be employed instead per implementation and design configuration. In the specific and non-limiting example shown in FIGS. 1B and 2A-C the wafer 162' the deformable layer 161' are of a circular disk shape, and the wafer 162' is structured and arranged to include 8 base elements 162. However, the fabrication technique shown in FIGS. 1B and 2A-C of course can used to manufacture wafers comprising any number of MEMSs/devices and having any other suitable shape and dimensions.

FIGS. 3A to 3E schematically illustrate structures and construction of fluidic MEMS 30 according to some possible embodiments comprising a multilayered fluid flow structure 10 including top and bottom elongated shell elements, 33 and 34 respectively, configured to be attached one to the other and form an enclosure for packaging top and bottom fluid channel portions, 31 and 32 (also referred to herein as connector portions), respectively. The top shell element 33 comprises an elongated open passage formed along its length and extending between the threading portions 33*a* and 33*b* formed at the extremities thereof, a top central window 33*p* that opens into the elongated open passage, and two lateral central cuts 33*r* passing through the side walls of the shell element 33 all the way into the elongated open passage.

The bottom shell element 34 comprises an elongated open passage formed along its length, extending between threading portion 34*a* and 34*b* formed at the extremities thereof, a bottom central window 34*p* that opens into the elongated open passage, and two central lateral cuts 34*r* passing through the side walls of the shell element 34 all the way into the elongated open passage.

As seen, except for the threading portions, 33*a*-33*b* and 34*a*-34*b*, the top and bottom shell elements 33 and 34 can be substantially symmetric about the plane of their connection where lateral edges of their elongated open passage reside.

The top fluid channel portion 31 comprises two fluid port portions 31*a* and 31*b* extending from its extremities towards its center. Each of the fluid port portions 31*a* and 31*b* comprises a central open channel extending along its length from the extremities towards the center of the top fluid channel portion 31, wherein a partition portion 31*n* (also referred to herein restrictor portion) is formed to partition between the two open channels. The fluid port portions 31*a* and 31*b* are connected to a central hub element 31*t* configured to snugly fit into the top central window 33*p* of the top shell element 33. The central hub element 31*t* comprises a cavity 31*c* located above and in fluid communication with the open channels of the fluid port portions 31*a* and 31*b*, a top opening 31*p* that opens into cavity 31*c*, and two lateral shoulders 31*s* configured to snugly fit into the lateral cuts 33*r* formed in the lateral walls of the shell element 33.

The bottom fluid channel portion 32 comprises two fluid port portions 32*a* and 32*b* extending from its extremities towards its center. Each of the fluid port portions 32*a* and 32*b* comprises a central open channel extending along its length from the extremities towards the center of the bottom fluid channel portion 32, wherein a partition portion 32*n* is formed to partition between the two open channels. The fluid port portions 32*a* and 32*b* are connected to a central hub element 32*t* configured to snugly fit into the bottom central window 34*p* of the bottom shell element 34. The central hub element 32*t* comprises two lateral shoulders 32*s* configured to snugly fit into the lateral cuts 34*r* formed in the lateral walls of the shell element 34.

Each fluid port portion can be configured as a frusta-conical element halved along its length, bored along its central axis to form the open channel passing along the central axis, and that gradually taper from the center of the fluid channel portion towards the extremity of the fluid port portion. This way, the fluid port portion 31*a* of the fluid channel portion 31 and the fluid port portion 32*a* of the fluid channel portion 32 are substantially symmetric about the plane of their connection, where lateral edges of their open channels reside. Similarly, the fluid port portion 31*b* of the fluid channel portion 31 and the fluid port portion 32*b* of the fluid channel portion 32 are substantially symmetric about the plane of their connection, where lateral edges of their open channels reside.

When the shell elements, 33 and 34, with their respective fluid channel portions 31 and 32, are attached one to the other, an elongated passage is formed by their elongated open passages that enclose the fluid channel portions 31 and 32 thereinside immobilized by the central hub elements and lateral shoulders of the fluid channel portions 31 and 32, that snugly fit into the respective central windows and lateral cuts of the shell elements 33 and 34. In this assembled state the open channels of the fluid channel portions 31 and 32 form two respective fluid lumens a and b, each sealed along its length, and two respective male connectors 31*a*-32*a* and 31*b*-32*b* are also formed, each having a frusta-conical shape tapering towards the extremity of the fluid flow structure 10.

As seen in FIG. 3D, in the assembled state, the partition portions 31*n* and 32*n* of the fluid channel portions 31 and 32 are attached one to the other to form a partition 31*n*-32*n* sealably partitioning between the fluid lumens a and b. In this way a continuous fluid passage 37 is formed along the device 30 extending along the sealed lumen a formed by the fluid port portions 31*a* and 32*a*, passing through the cavity 31*c* formed inside the central hub 31*t*, and therefrom extending along the sealed lumen b formed by the fluid port portions 31*b* and 32*b*. As shown in FIG. 3C, after assembling the fluid flow structure 10 a sealing element 36' is sealably attached over the top surface of the top shell element 33, to sealably close the top opening 31*p* of the central hub element 31*t* and place thereover sensor and/or circuitry elements 36*i* formed thereon.

As seen in FIGS. 3C and 3D, when all parts of the fluid flow structure 10 are assembled, the threading portions 33*a* and 34*a* are joined to form connector threading that can be used to secure a fluid connector to the connector 31*a*-32*a*, and similarly the threading portions 33*b* and 34*b* are joined to form connector threading that can be used to secure a fluid connector to the connector 31b-32b. The device 30 can be connected to a fluid source either by the connector 31a-32a formed at one side thereof, or by the connector 31b-32b at the other side, for flowing a fluid through the fluid passage 37, thereby filling the cavity 31c with the streamed fluid and causing it to interact with the sealing element 36' sealing its top opening 31p. The sensor elements/circuitries 36i patterned/mounted on the sealing element 36' can be used to measure properties of the liquid substance introduced into the cavity 31c.

Figure 7A:
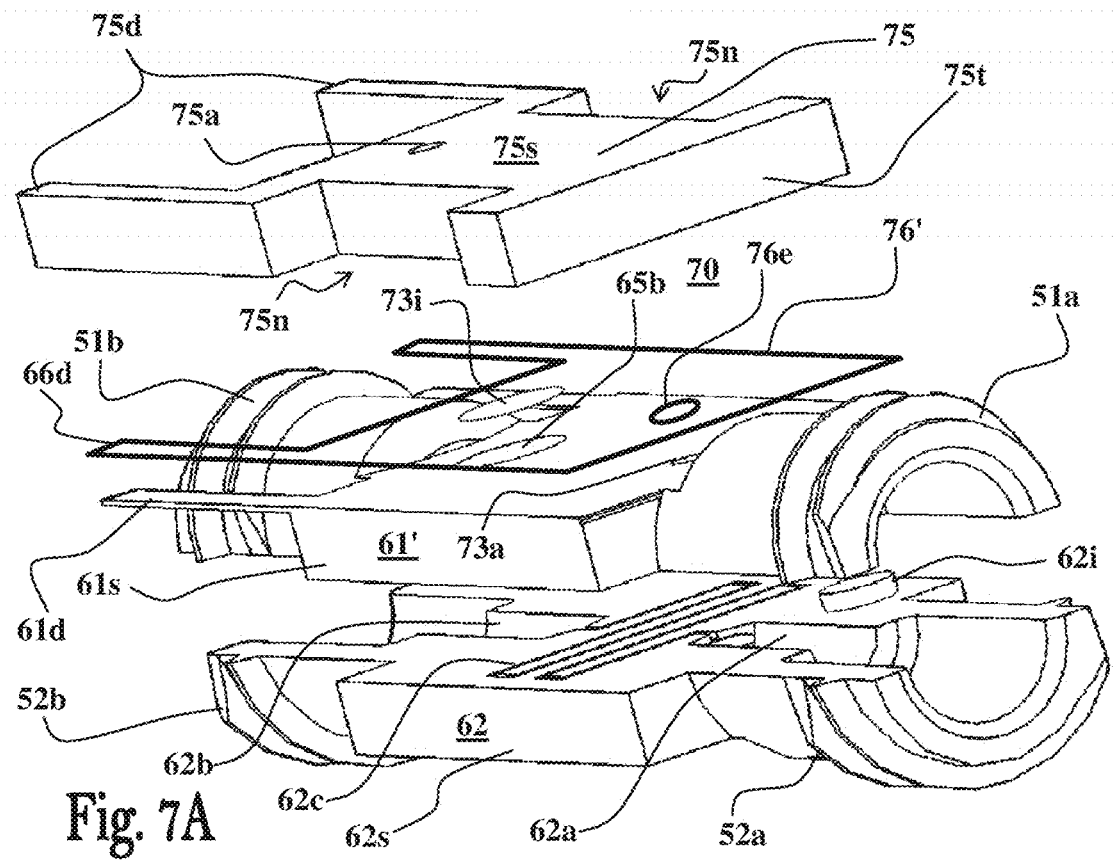
FIGS. 7A to 7E schematically illustrate fluidic MEMS of some possible embodiments comprising a differential flow sensing element, wherein FIGS. 7A and 7B respectively show an exploded perspective view and an exploded perspective sectional view of the preassembled fluidic MEMS.
Figure 7B:
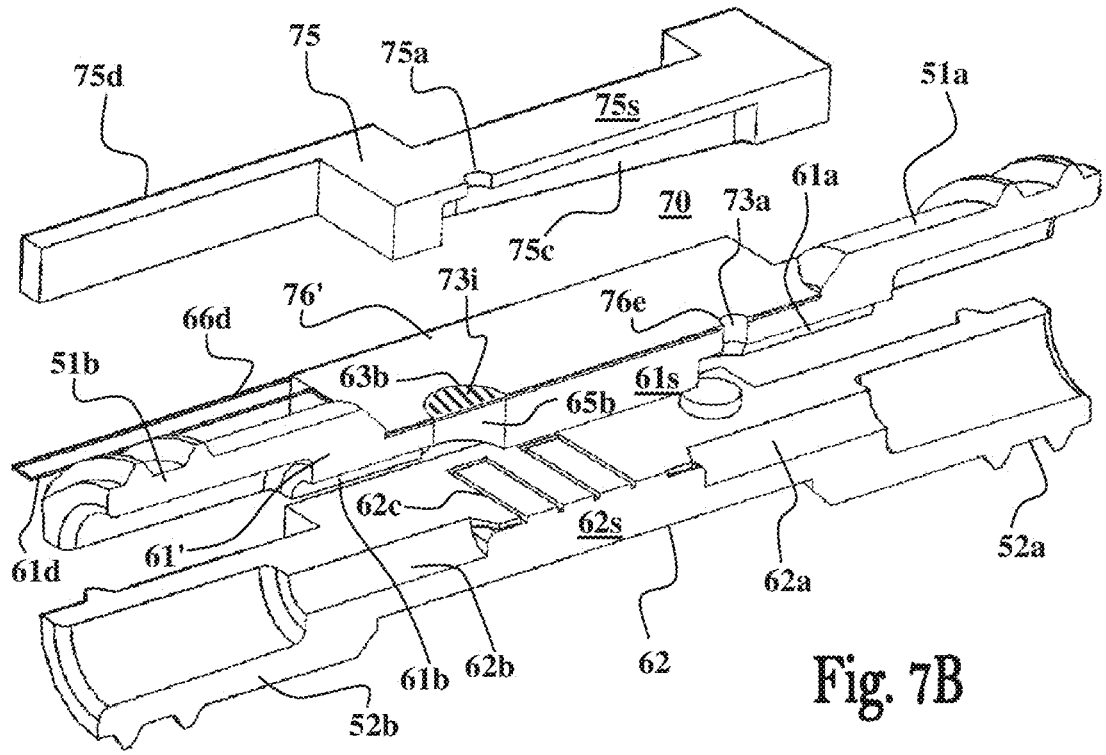
Figure 7C:
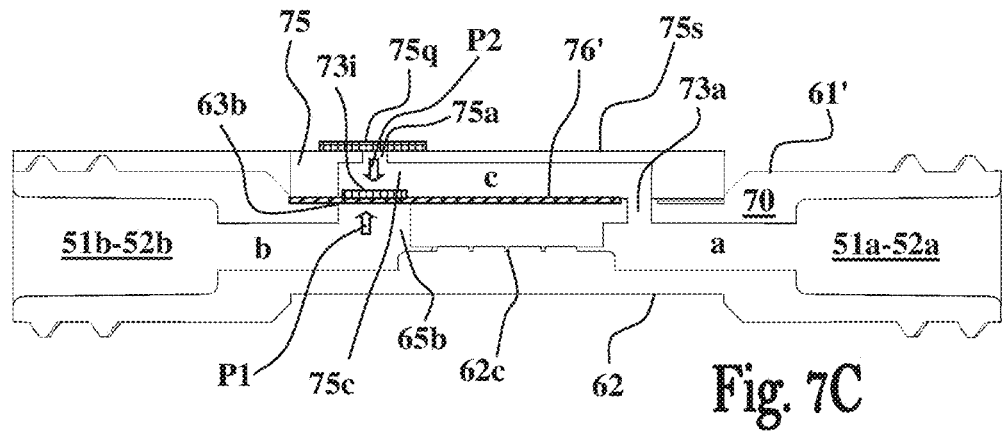
Figure 7D:
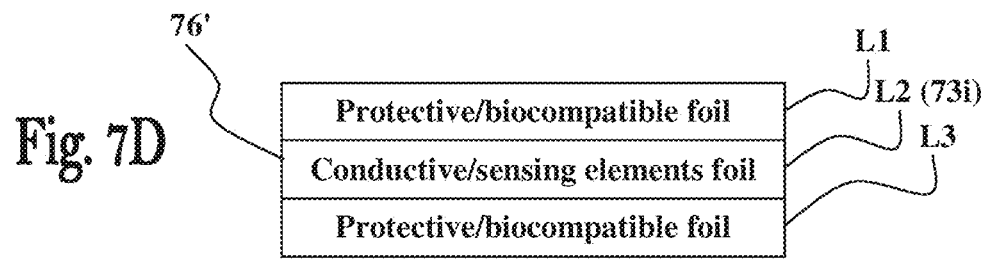

In some embodiments the sealing element comprises sensors elements configured to contact the fluid introduced into the cavity 31c and measure properties thereof (e.g., using electrodes), such as, but not limited to pH level, electrical conductivity, and suchlike. Additionally, or alternatively, the sealing element 36' can comprise contactless sensor elements (not shown) configure to measure properties of the liquid in the cavity 31c, such as, but not limited to, temperature of the liquid (e.g., using piezoelectric sensing elements). Optionally, and in some embodiments preferably, the sealing element 36' is a multilayered structure, such as illustrated in FIG. 7D.

Optionally, and in some embodiments preferably, the sealing element 36' is elastically (or flexible) deformable element (thin foil/film) comprising one or more piezoelectric elements configured to measure forces applied over the sealing element 36' as it is deformed in response to the fluid streamed through the device 30, that can be used to determine fluid pressure and/or flow rate. In some embodiments the sealing element 36' comprises two or more different sensors configured to measure two or more different properties of the liquid.

As seen and described above, the device 30 is assembled from four parts (also referred to herein as body elements) and a sealing elements attached over the top opening 31p, and each one of the different parts, 31, 32, 33 and 34, can be easily fabricated by any conventional 3D object production technique without presenting undercuts and/or need to form partially or fully closed cavities.

Optionally, and in some embodiments preferably, each of the different parts of the device 30 is fabricated as an integral part of an array of such parts configured to be attached to arrays of parts to be attached thereto, such that four different arrays of parts are formed for attachment one to other to from a layered structure. With reference to FIG. 3E, in this embodiment each top fluid channel portion 31 is fabricated as an integral part of an array of top fluid channel portion parts A31, each bottom fluid channel portion 32 is fabricated as an integral part of an array of bottom fluid channel portion parts A32, each top shell element 33 is fabricated as an integral part of an array of top shell elements A33, and each bottom shell element 34 is fabricated as an integral part of an array of such bottom shell elements A34.

A plurality of fluid flow structures 10 of MEMSs/devices 30 are assembled by attaching the array of top shell elements A33 to the array of top fluid channel portion parts A31 to form a top assembly, attaching the array of bottom shell elements A34 to the array of bottom fluid channel portion parts A32 to from a bottom assembly, and attaching the top assembly to the bottom assembly. In some embodiments the array of top shell elements A33 is arranged in an upper support frame 33f having a plurality fastening pins 33i protruding downwardly therefrom, and the array of bottom shell elements A34 is arranged in a bottom support frame 34f having a respective plurality of fastening sockets 34s formed in upper faces thereof. The plurality of fastening sockets 34s of the bottom support frame 34f are configured to snugly receive the plurality of fastening pins 33i of the upper support frame 33f, to thereby firmly encase the different layers of the structure attached one to other and form a wafer 39 (in FIG. 3F) comprising an array of the fluid flow structures 10 of MEMSs/devices 30.

It should be understood that the arrays of parts A33, A31, A32 and A34, can be attached one to other in any suitable order, and not limited to the above-provided example. The arrays of parts A33, A31, A32 and A34, can be attached one to the other as shown in FIGS. 3E and 3F using any suitable techniques, such as, but not limited to, gluing, laser welding, ultrasonic welding, hot welding, and suchlike. The reasons to construct the fluid flow structures 10 of MEMSs/devices 30 in such multilayered structure is derived from the complexity of the final device, and how it is arrayed. The motivation in this specific and non-limiting example arises at least in part from the following:

in case the wafer 39 is fabricated by injection molding, the wafer 39 cannot be built from one or two parts because undercuts or closed empty volumes are inevitably present in such designs; and in case the wafer 39 is fabricated by 3D printing (SLA, DLP, SLS, etc.), while undercuts can be printed, there is an inevitable need to clean uncured material, as it is impossible to otherwise print closed empty volumes in such techniques.

It is important to note that this specific and non-limiting example the wafer 39 of fluid flow structures 10 of MEMSs/devices 30 cannot be built as one integral (monolithic) part by 3D printing, but from at least two parts/layers (e.g., such as the above-described upper and bottom assemblies), since such designs inevitably require drainage of uncured materials and drilling of holes and/or support structures.

After assembling the wafer 39 of fluid flow structures 10 of MEMSs/devices 30 a sealing sheet 36 is sealably attached over the upper side of the wafer 39. The sealing sheet 36 comprises a respective array of sensor units/circuitries 36i aligned so as to place each sensor unit/circuitry 36i of the sealing sheet 36 precisely over a respective top opening 31p of one of the fluid flow structures 10 of MEMSs/devices 30. The sealing sheet 36 can be attached to the upper face of the wafer 39 by gluing, laser welding, lamination, ultrasonic welding or hot welding. Alternatively, the array of sensor units/circuitries 36i can be patterned (or mounted) on the sealing sheet/foil 36 after it is attached to layered structure. Thereafter, the MEMSs/devices 30 can be diced/cut out from the wafer 39 using any suitable dicing technique known in the art.

In the different wafer embodiments disclosed herein, the sensor units/circuitries 36i can be calibrated before the dicing, or after the dicing. In some embodiments all of the sensor units/circuitries 36i placed on the wafer are calibrated in a single calibration step by applying to the finalized wafer of MEMSs/devices the same calibration conditions at the same time, using any of the wafer calibration techniques described in U.S. Provisional Patent application No. 62/470/407, of the same applicant hereof, the disclosure of which is incorporated herein by reference.

Figure 4A:
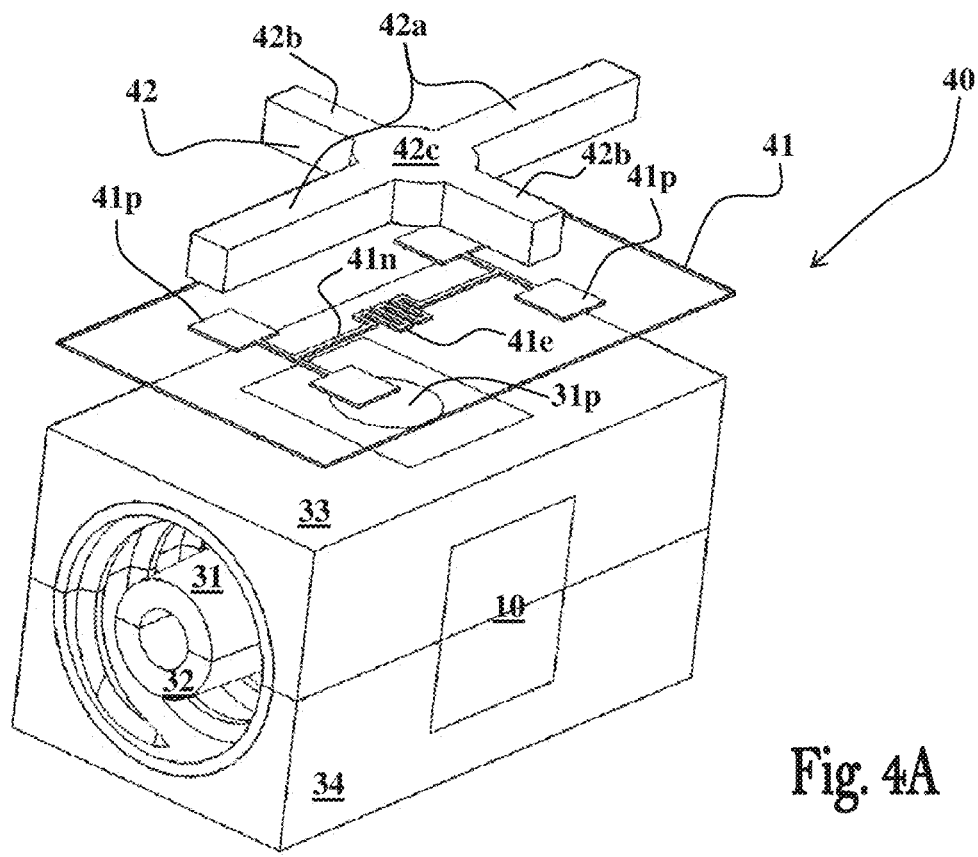
Figure 4B:
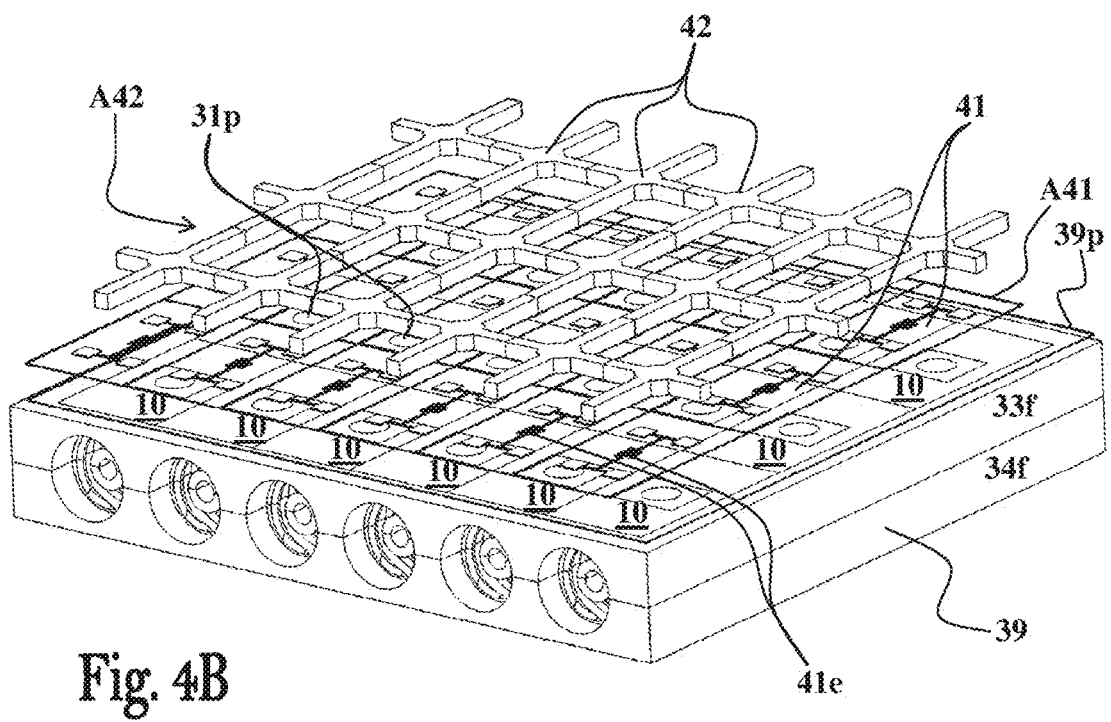

FIGS. 4A and 4B schematically illustrate fluidic MEMS/device 40 of some possible embodiments configured for temperature measurements. In this specific and non-limiting example the fluid flow structure 10 is of substantially the same fluid flow structure described hereinabove with reference to FIGS. 3A to 3F. The top opening 31p of the fluid flow structure 10 is sealed by a sensor sheet 41 having at least one temperature sensor 41e patterned or mounted thereon such that it is precisely placed over the top opening 31p of the fluid flow structure 10. The sensor sheet 41 further comprises at least two contact pads 41$p$, electrically coupled to the temperature sensor 41$e$ by conducing lines 41$n$ patterned thereon. In this specific and non-limiting example the sensor sheet 41 comprises four contact pads 41$p$, where one pair of contact pads 41$p$ is electrically coupled to one side of the temperature sensor 41$e$ by conducting lines 41$n$, and another pair of the contact pads 41$p$ is electrically coupled by conducting lines 41$n$ to the other side of the temperature sensor 41$e$, which can be used to minimize of electrical resistance differences by conducting the measurements via the pairs of contact pads 41$p$ provided at the extremities of the temperature sensor 41$e$.

Optionally, and in some embodiments preferably, the temperature sensor 41$e$ is a type of resistive temperature detector (RTD) made of an electrically conductive material (e.g. NiCr, Platinum, copper, gold, etc.) having a periodic zigzagged structure, or rectangular-wave structure, or any other wavy structure. The temperature sensor 41$e$ can be patterned using metal deposition techniques (evaporation, sputtering, electroplating, electroless plating) or lamination processes combined with lithography processes, and the contact pads 41$p$ and the conducting lines 41$n$ can be patterned using NiCr, Platinum, copper, gold, etc. The sensor sheet 41 can be made from a thin film or foil made of polymeric material (e.g., polyimide, polycarbonate, peek, ultem, polyurethane, etc.) having good thermal coupling properties (i.e., high thermal conductivity), and it may be either rigid or flexible/elastic, per implementation requirements.

After attaching the sensor sheet 41 to the upper surface of the fluid flow structure 10, a rigid shielding element 42 is attached thereon to substantially immobilize and prevent deformations of the sensor sheet 41 portion located over the top opening 31$p$ when pressure forces are applied thereon when fluids are introduced into the cavity of the fluid flow structure 10, and to provide thermal insulation from the external environment. The shielding element 42 is configured to substantially prevent measurements errors that can be induced due to deformations of the temperature sensor 41$e$ patterned on the sensor sheet 41, and due to temperature differences between the fluid substance introduced into the cavity 31$c$ and the external environment.

The shielding element 42 can have any shape suitable to substantially cover the top opening 31$p$ and prevent deformations of the sensor sheet 41, and it can be fabricated from any suitable material having poor/low thermal conductivity properties. Optionally, and in some embodiments preferably, the shielding element 42 has a type of celtic-cross shape having an elongated arm 42$a$ extending substantially along the length of the fluid flow structure 10, two short transversal arms 42$b$ extending in sideway directions from the center of, and substantially perpendicular to, the elongated arm 42$a$, and a central disk-shaped portion 42$c$ merging into the arms 42$a$ and 42$b$ at their connection area and substantially covering the top opening 31$p$ of the fluid flow structure 10. This configured is particularly advantageous to construct a plurality of fluidic MEMS s/devices 40 in a multilayered wafer form, as shown in FIG. 4B.

The wafer 39 of fluid flow structures 10 in FIG. 4B is substantially of the same multilayered structure shown in FIGS. 3E and 3F. In some embodiments a protective layer 39$p$ is applied over the top surface of the wafer 39, which can be implemented by a thin film or foil made of polymeric sheet/foil/film (e.g., polyimide, peek, ultem, polycarbonate, polyurethane) attached to the wafer 39 by laser welding, gluing, ultrasonic welding. An array of sensor sheets A41 is attached to the wafer 39 by laser welding, gluing, ultrasonic welding such that a respective sensor sheet 41 is placed over each one of the fluid flow structures 10 and a respective temperature sensor 41$e$ is precisely placed over each top opening 31$p$ of each fluid flow structures 10 of the wafer 39. After attaching the array of sensor sheets A41 to the wafer 39, an array of shielding elements A42 is attached to the wafer on top of the array of sensor sheets A41 such that a respective shielding element 42 is precisely placed over each temperature sensor 41$e$ of the array of sensor sheets A41, while substantially covering the respective top openings 31$p$. The finalized wafer, with or without the optional protective layer 39$p$, and with the arrays of sensor sheets A41 and shielding elements A42, can be then diced using any suitable dicing technique, to cut out the temperature measurement MEMSs/devices 40.

It is noted that the opening 31$p$ used with the temperature sensor 41$e$ can assume one of various different shapes, such as, but not limited to, rectangular, circular, oval, etc. For example, an elongated long and narrow rectangular-shaped opening 31$p$ will guarantee that less deformations of the sealing element 41 attached over the opening 31$p$ occur, than in circular configurations thereof.

FIGS. 5A to 5H schematically illustrate structure and construction of fluidic MEMS 55 of some possible embodiments comprising a male connector 31$b$-32$b$ and female connector 51$a$-52$a$. Optionally, and in some embodiments preferably, the male connector 31$b$-32$b$ and the female connector 51$a$-52$a$ are configured as Luer lock connectors, or any other type of quick connector structure e.g., barbed fittings, screw threading, or suchlike. The fluidic MEMS/device 55 comprises a multilayered fluid flow structure 50 assembled from top and bottom casing elements, 53 and 54 respectively, configured to be attached one to the other and form an enclosure for packaging top and bottom fluid channel portions, 51 and 52, respectively. The top and bottom casing elements 53 and 54 are generally "U"-shaped elements, each having two substantially parallel arms perpendicularly extending from a base section optionally having a threading portion extending substantially perpendicular to the plane of the parallel arms.

More particularly, the casing element 53 comprises the two parallel arms 53$r$ perpendicularly extending from the base section 53$b$ having the threading portion 33$b$ extending substantially perpendicular to the plane of the parallel arms 53$r$, and the casing element 54 comprises the two parallel arms 54$r$ perpendicularly extending from the base section 54$b$ having the threading portion 34$b$ extending substantially perpendicular to the plane of the parallel arms 53$r$. The casing elements 53 and 54 also comprise support extensions extending longitudinally from each one of the arms and configured to provide support for the multilayered fluid flow structure 50 and facilitate attachment of a sealing element 36' having one or more sensor elements/circuitries patterned/mounted thereon.

Figure 5E:
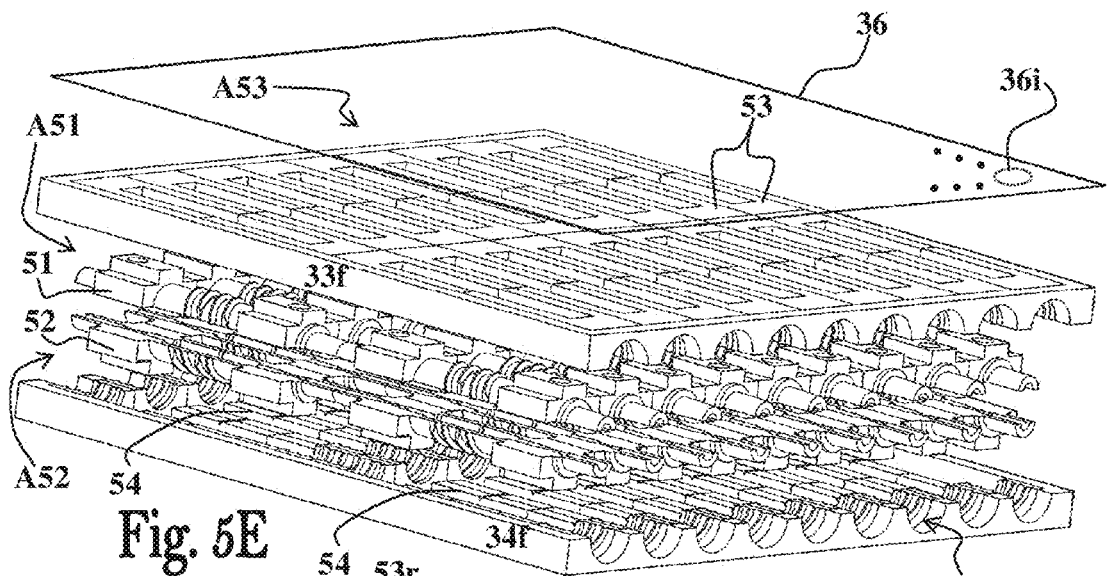
Figure 5F:
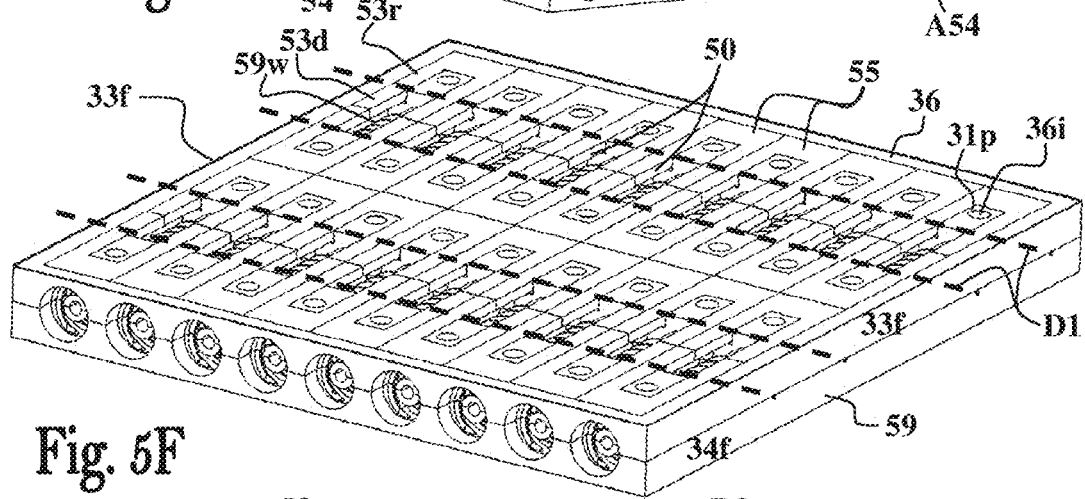
Figure 5G:
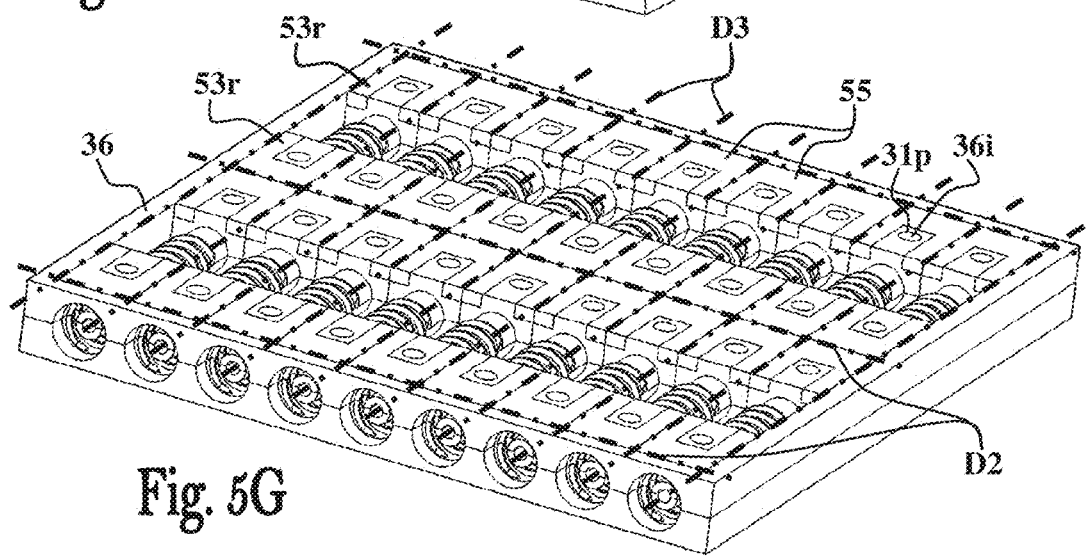

Particularly, the top casing element 53 comprises two elongated support extensions 53$d$ extending longitudinally from its parallel arms 53$r$ and configured to provide support for attachment of the sealing element 36' thereover, and the bottom casing element 54 comprises two elongated support extensions 54$d$ extending longitudinally from its parallel arms 54$r$ and configured to provide support to the multilayered fluid flow structure 50. The elongated support extensions 53$d$ and 54$d$ are also useful for the construction of an array of the fluid flow structure 50, as shown in FIGS. 5E to 5G, where they are also used for connecting between adjacently located casing elements. Optionally, and in some embodiments preferably, after assembling the fluid flow structure 50 and attaching the sealing element 36 thereover, the support extensions 53d and 54d are removed from the MEMS/device 55 using any suitable partial depth (not through) dicing technique (e.g., laser cutting, mechanical sawing, hot wire cutting, etc.), to obtain the final MEMS/device configuration readily operable for use shown in FIGS. 5C and 5D.

When the casing elements 53 and 54 are attached one to the other the threading portions 53b and 54b form a circular passage comprising a complete threading structure on inner surface thereof, and configured to enclose a male connector 31b-32b assembled by the fluid channel portions, 51 and 52. In the assembled state the parallel arms 53r of casing element 53 and the parallel arms 54r of casing element 54 are aligned in two parallel plains, and thus define respective top and bottom socket, 53s and 54s respectively, and two lateral sockets 50s.

As seen, except for the threading portions 34a-34b the top and bottom casing elements 33 and 34 can be substantially symmetric about the plane of their connection i.e., a plane substantially centered between the planes of the parallel arms 53r and 54r.

The top fluid channel portion 51 comprises a female connector portion 51a and a male connector portion 31b, extending from its extremities towards its center. Each of the connectors portions 51a and 31b comprises a central open channel extending along its length from the extremities towards the center of the top fluid channel portion 51, wherein a partition portion 51n is formed to partition between the two open channels. The fluid port portions 51a and 31b are connected to a central hub element 51t configured to snugly fit into the top socket 53s in abutment to the base section 53b of the top casing element 53. The central hub element 51t comprises a cavity 51c located above and in fluid communication with the open channels of the fluid port portions 31a and 31b through respective vertical lumens 51i and 51j partitioned by the partition portion 51n passing therebetween, a top opening 31p that opens into the cavity 51c, and two lateral shoulders 32s.

The bottom fluid channel portion 52 comprises corresponding female connector portion 52a and male connector portion 32b extending from its extremities towards its center. Each of the connector portions 52a and 32b comprises a central open channel extending along its length from the extremities towards the center of the bottom fluid channel portion 52, wherein a partition portion 52n is formed to partition between the two open channels. The connector portions 52a and 32b are connected to a central hub element 52t configured to snugly fit into the bottom socket 52s of the bottom casing element 34 in abutment to the base section 54b of the bottom casing element 54. The central hub element 52t comprises two lateral shoulders 32s.

The male connector portions 31b and 32b can be configured as a frusta-conical elements halved along their lengths, bored along their central axis to form the open channel passing along the central axis, and that gradually taper from the center of their fluid channel portions towards the extremity of the male connector portion. The male connector portions 31b and 32b are thus substantially symmetric about the plane of their connection, where lateral edges of their open channels reside. The female connector portion 51b of the fluid channel portion 51 and the female connector portion 32b of the fluid channel portion 52 have a generally halved-cylinder shape that are substantially symmetric about the plane of their connection, where lateral edges of their open channels reside.

When the casing elements, 53 and 54, with their respective fluid channel portions 51 and 52, are attached one to the other, the lateral shoulders 31s and 32s of the fluid channel portions 51 and 52 are joined to form two lateral fastening steps 31s-32s snugly received in the lateral sockets 50s. In this way, in the assembled state the fluid channel portions 51 and 52 are joined to form an assembly comprising the male connector 31b-32b enclosing fluid lumen b sealed along its length, and the female connector 51a-52a leading to fluid lumen a sealed along its length, and the assembly is held immobilized by the central hub elements and lateral fastening steps of the fluid channel portions 51 and 52, that snugly fit into their respective sockets. The male connector 31b-32b has a frusta-conical shape tapering towards the extremity of the fluid flow structure 50, and the female connector 51a-52b has a generally cylindrical shape.

As seen in FIG. 5D, in the assembled state, the partition portions 51n and 52n of the fluid channel portions 51 and 52 are attached one to the other to form a continuous partition 51n-52n sealably partitioning between the fluid lumens a and b. In this way a continuous fluid passage 57 is formed along the device (55) extending along the sealed lumen b formed by the fluid port portions 31b and 32b, passing upwardly through the lumen 51i into the cavity 31c and therefrom downwardly through the lumen 51j that are formed in the central hub 51t, and therefrom extending along the sealed lumen a. As shown in FIG. 5D, after assembling the fluid flow structure 50 a sealing element 36' is sealably attached over the top surface of the top casing element 53, to sealably close the top opening 31p of the central hub element 31t and place thereover sensor and/or circuitry elements 36i formed/mounted thereon.

As seen in FIGS. 5C and 5D, when all parts of the fluid flow structure 50 are assembled, the threading portions 33b and 34b are joined to form connector threading that can be used to secure a fluid connector to the formed male connector 31b-32b. The device 55 can be connected to a fluid source either by the male connector 31b-32b formed at one side thereof, or by the female connector 51a-52a formed at the other side, for flowing a fluid through the fluid passage 57, thereby filling the cavity 51c with the streamed fluid and causing it to interact with the sealing element 36' sealing its top opening 31p. The sensor elements/circuitries 36i patterned/mounted on the sealing element 36' can be used to measure properties of the liquid substance introduced into the cavity 31c.

In some embodiments the sealing element comprises sensors elements configured to contact the fluid introduced into the cavity 31c and measure properties thereof (e.g., using electrodes), such as, but not limited to pH level, electrical conductivity, and suchlike. Additionally, or alternatively, the sealing element 36' can comprise contactless sensor elements (not shown) configured to measure properties of the liquid in the cavity 31c, such as, but not limited to, temperature of the liquid (e.g., using piezoelectric sensing elements). Optionally, and in some embodiments preferably, the sealing element 36' is elastically (or flexible) deformable element (thin foil/film) comprising one or more piezoelectric elements configured to measure forces applied over the sealing element 36' as it is deformed in response to the fluid streamed through the device 55, that can be used to determine fluid pressure and/or flow rate. In some embodiments the sealing elements comprises two or more different sensors configured to measure two or more different properties of the liquid.

As seen and described above, the device 55 is assembled from four parts (also referred to herein as body elements)

and a sealing elements attached over the top opening 31p, and each one of the different parts, 51, 52, 53 and 54, can be easily fabricated by any conventional 3D object production technique without presenting undercuts and/or need to form partially or fully closed cavities.

Optionally, and in some embodiments preferably, each of the different parts of the device 55 is fabricated as an integral part of an array of such parts configured to be attached to arrays of parts to be attached thereto, such that four different arrays of parts are formed for attachment one to other in to from a layered structure. With reference to FIG. 5E, in this embodiment each top fluid channel portion 51 is fabricated as an integral part of an array of top fluid channel portion parts A51, each bottom fluid channel portion 52 is fabricated as an integral part of an array of bottom fluid channel portion parts A52, each top casing element 53 is fabricated as an integral part of an array of top shell elements A53, and each bottom casing element 54 is fabricated as an integral part of an array of such bottom casing elements A54.

As seen in FIG. 5F, a plurality of fluid flow structures 50 of MEMSs/devices 55 are assembled by attaching the array of top casing elements A53 to the array of top fluid channel portion parts A51 to form a top assembly, attaching the array of bottom casing elements A54 to the array of bottom fluid channel portion parts A52 to from a bottom assembly, and attaching the top assembly to the bottom assembly. In some embodiments the array of top casing elements A53 is arranged in an upper support frame 33f and the array of bottom shell elements A34 is arranged in a bottom support frame 34f. The array of top and bottom casing elements are attached one to the other to encase the different layers of the fluid flow structures attached one to other and form a wafer 39 comprising an array of the fluid flow structures 50 of the MEMSs/devices 55.

In this specific and non-limiting example an array of 4×9 MEMSs/devices 55 is constructed in the wafer 59, and the fluid flow structure is arranged such that at each side of the array the first two rows of 9 MEMSs/devices 55 are connected one to the other by their female connectors, and the two central rows of 9 MEMSs/devices 55 are connected one to the other by their male connectors. It is however noted that in possible embodiments the wafer may be configured to construct an array consisted of a single row, or of a single column, of the MEMSs/devices 55

It is noted that the arrays of the parts A53, A51, A52 and A54, can be attached one to other in any suitable order, and not limited to the above-provided example. The arrays of parts A53, A51, A52 and A54, can be attached one to the other as shown in FIGS. 5E and 5F using any suitable technique, such as, but not limited to, gluing, laser welding, ultrasonic welding, hot welding, and suchlike. as in the previous embodiments, in case the wafer 59 is fabricated by injection molding, the wafer 59 cannot be built from one or two parts because undercuts are inevitably present in such designs, and in case the wafer 59 is fabricated by 3D printing (SLA, DLP, SLS, etc.), while undercuts can be printed, there is an inevitable need to clean uncured material, as it is impossible to otherwise print closed empty volumes in such techniques. It is also noted that this specific and non-limiting example the wafer 59 of fluid flow structures 50 of MEMSs/devices 55 cannot be built as one integral (monolithic) part, but from at least two parts/layers (e.g., such as the above-described upper and bottom assemblies), since such designs inevitably require drainage of uncured materials and drilling of holes.

After assembling the wafer 59 of fluid flow structures 50 of MEMSs/devices 55 a sealing sheet 36 (e.g., thin foil/film) is sealably attached over the upper side of the wafer 59. The sealing sheet 36 comprises a respective array of sensor units/circuitries 36i aligned so as to place each sensor unit/circuitry 36i of the sealing sheet 36 precisely over a respective top opening 31p of one of the fluid flow structures 50 of MEMSs/devices 55.

As seen, the sealing sheet 36 covers the elongated openings 59w formed in the wafer 59 over the female connectors between the elongated support extensions 53d of the top casing element 53. In some embodiments the sealing sheet is attached to the wafer 59 before deposition of the conductive/sensing elements 36i, and in this case the sensors/circuitries 36i can be applied on a flat wafer covered by the sealing sheet 36, which thus allows use of standard lithography and/or metal deposition techniques.

The sealing sheet 36 can be attached to the upper face of the wafer 59 by gluing, laser welding, ultrasonic welding or lamination. Thereafter, the MEMSs/devices 55 can be diced/cut out from the wafer 59 in a two steps dicing process using any suitable dicing technique known in the art, as illustrated in FIGS. 5F and 5G.

Particularly, the dicing process comprises in some embodiments a preliminary dicing step illustrated by dashed lines D1 in FIG. 5F, in which partial cuts D1 are transversally applied along the top side and the bottom side (not shown) of the wafer 59 in a relatively short depth sufficient to only cut off the support top and bottom extensions 53d and 54d and remove portions of the sealing sheet located over the elongated openings 59w. Accordingly, the partial cuts D1 don't pass all the way through the wafer 59, and in some embodiments their depths is in the range of 0.01% to 25% of the wafer thickness. In further dicing steps pass through cuts are then applied, as illustrated by the dashed-dotted lines D2 and D3 shown in FIG. 5G, to remove the MEMSs/devices 55 from the wafer 59. In these dicing steps one or more traversal pass through cuts D2 are applied to separate the the rows of the MEMSs/devices 55 one from the other, and one or more longitudinal pass through cuts D3 are applied to separate the columns of the MEMSs/devices 55 one from the other.

Figure 5H:
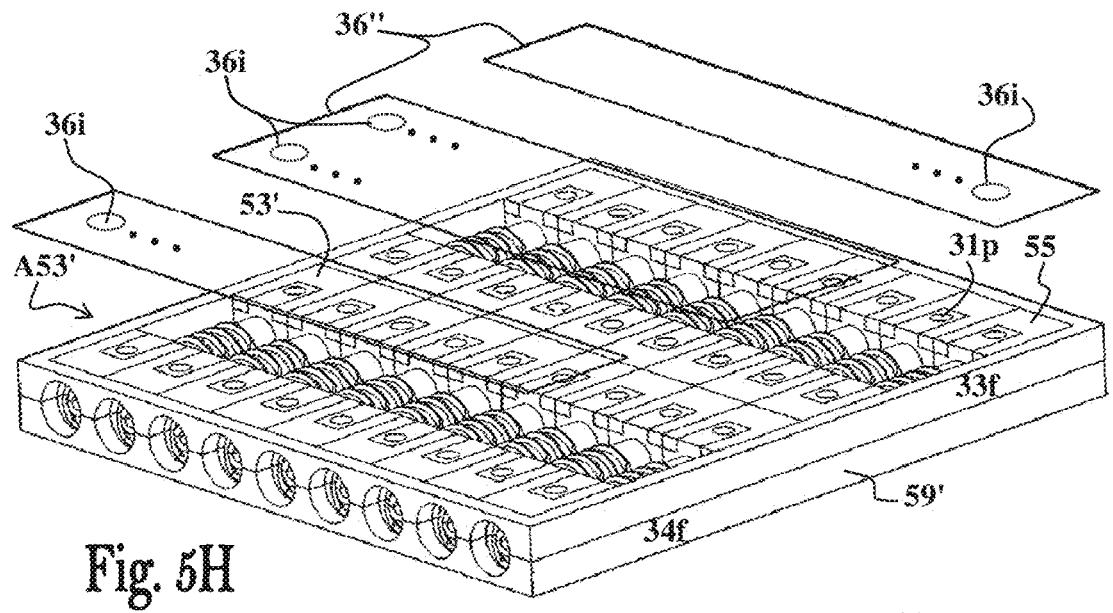

FIG. 5H shows a possible embodiment wherein a wafer 59' comprising the array of MEMSs/devices 55 is assembled using an array A53' of top casing elements 53' fabricated without the elongated support extensions. In this embodiment a plurality of sealing sheets 36" are used to seal the top openings 31p i.e., the sealing sheets 36" transversally cover a portion of a row, or portions of two rows, of the MEMSs/devices 55 of the wafer, comprising the base sections 53b, top parallel arms 53r and central hubs 31t, without covering the elongated openings 59w. As seen, in this specific and non-limiting example the MEMS devices 55 do not have the elongated support extensions parallel arms 53d and 54d, and thus the three separated sealing sheets 36" are used, wherein each of the two sealing sheets 36" applied over the first and last rows of MEMSs/devices 55 comprises a single row of sensor and/or circuitry elements 36i, and the sealing sheet 36" applied over the second and third rows of MEMSs/devices 55 comprises corresponding two rows of sensor and/or circuitry elements 36i.

Figure 6A:
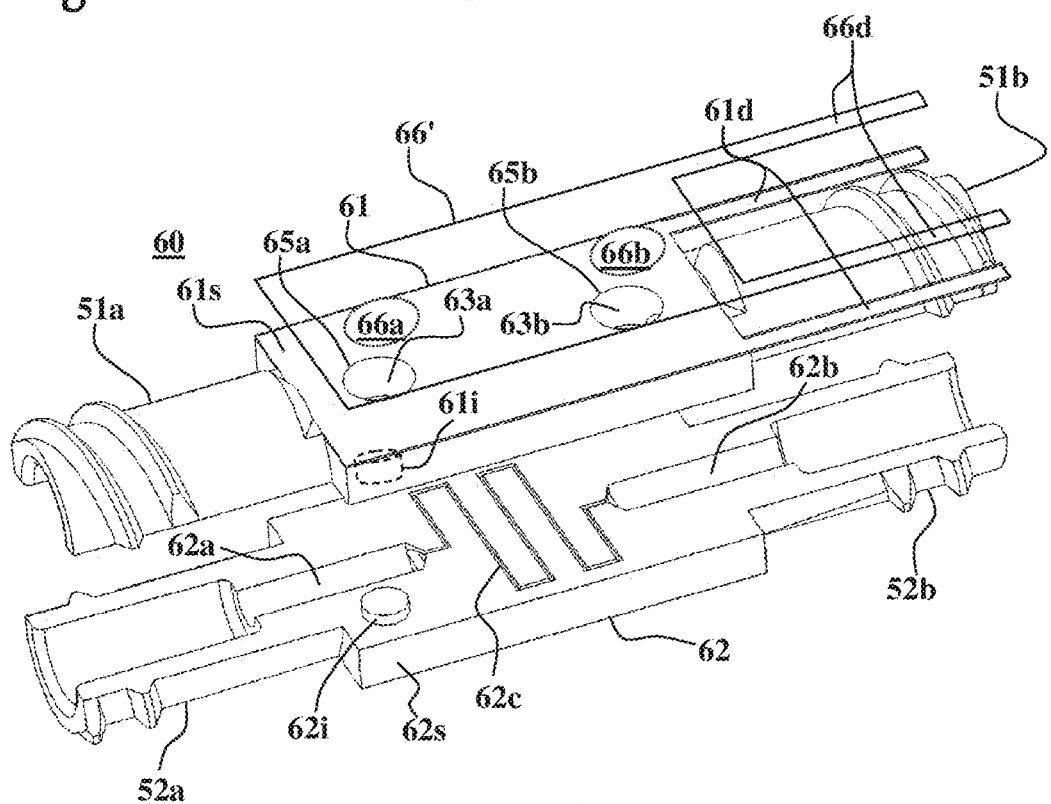

FIGS. 6A to 6C schematically illustrate structure and construction of a fluidic MEMS/device 60 of some possible embodiments comprising two female connectors 51a-52a and 51b-52b. The MEMS/device 60 comprises a top and bottom elongated elements 61 and 62 configured to be attached one to the other and form the two female connectors 51a-52a and 51b-52b and a fluid passage along the length of the MEMS/device 60. Optionally, and in some embodiments preferably, the female connectors 51a-52a and 51b-52b are Luer lock connectors or any other type of quick connector structure (e.g., barbed fittings, screw threading, or suchlike).

The top elongated element 61 comprises first and second female connector portions, 51a and 51b respectively, at its extremities and having threading portions formed thereon, and a base portion 61s from which the first and second female connector portions 51a and 51b longitudinally extend. A first open channel 61a is formed along a bottom portion of the top element 61 longitudinally extending from the first female connector portion 51a and communicating with a first cavity 63a formed in the base portion 61s and having a first opening 65a at the upper side of the base portion 61s. A second open channel 61b is formed along a bottom portion of the top element 61 longitudinally extending from the second female connector portion 51b and communicating with a second cavity 63b formed the in base portion 61s and having a second opening 65b at the upper side of the base portion 61s.

The base portion 61s of the top element 61 can further comprise two support arms 61d extending longitudinally therefrom at the sides and in parallel to one of the female connector portions, and configured to provide support for extension arms 66d of a sealing element 66' configured to attach to the upper side of the top element 61. In this example the support arms 61d extend along sides of female connector portion 51b, and the extremities of the support arms 61d are substantially aligned with the extremity of the female connector portion 51b. The sealing element 66' is configured to seal the openings 65a and 65b formed in the base portion 61s, and comprises sensor and/or circuitry elements 66a configured to be precisely placed over the opening 65a, and sensor and/or circuitry elements 66b configured to be precisely placed over the opening 65b.

The bottom elongated element 62 comprises first and second female connector portions, 52a and 52b respectively, at its extremities and having threading portions formed thereon, and a base portion 62s from which the first and second female connector portions 52a and 52b longitudinally extend. A first open channel 62a is formed along an upper portion of the bottom element 62 longitudinally extending from the first female connector portion 52a and communicating with a first end of a slender fluid channel 62c transversally zigzagged (e.g., having a rectangular wave pattern) along a surface of the upper side of the bottom element 62. A second open channel 62b is formed along an upper portion of the bottom element 62 longitudinally extending from the second female connector portion 52b and communicating with a second end of the slender fluid channel 62c.

The base portion 62s of the bottom elongated element 62 can comprise one or more fastening pins 62i configured to be snugly received in corresponding one or more fastening sockets 61i formed in the base portion 61s of the top elongated element 61 when the top and bottom elements are attached one to the other. In possible embodiments the fastening pins can be in the top element and the fastening sockets in the bottom element.

When the elongated top and bottom portions are attached one to the other the female connector portions 51a and 52a at one side of the elongated elements are joint to form the female connector 51a-52a, and their threading portions are also joined to form a complete threading structure cable of securing a corresponding male connector to the female connector 51a-52a. Likewise, the female connector portions 51b and 52b at the other side of the elongated elements are joint to form the female connector 51b-52b, and their threading portions are also joined to form a complete threading structure cable of securing a corresponding male connector to the female connector 51b-52b. In the assembled state the open channels 61a and 62a respectively extending from the female connector portions 51a and 52a are joined to form a fluid lumen La sealed along its length, a portion of the base portion 61s of the top element 61 sealably cover the slender fluid channel 62c, and the open channels 61b and 62b respectively extending from the female connector portions 51b and 52b are joined to form a fluid lumen Lb sealed along its length.

The sealing element 66' is then attached over the top elongated element 61 such that its arm extensions 66d are placed over the two support arms 61d of the base portion, and such that the first sensor and/or circuitry elements 66a are precisely positioned over the first opening 65a and the sensor and/or circuitry elements 66b are precisely positioned over the second opening 65b.

The cross sectional area of the slender channel 62c is substantially smaller then and cross sectional areas of the lumens La and Lb, which have approximately the same cross area. In some embodiments the cross sectional area of the slender channel 62c is about 1000 to 1.5 times smaller than the cross sectional area of the lumen La and/or Lb, and its length can be set according to cross-sectional area of the slender channel 62c itself and the fluid flow rate which need to be measured. Thus, when a fluid is streamed through the MEMS/device 60, a pressure difference evolves between the first and second cavities 63a and 63b, that can be measured by the respective first and second sensor circuitry elements 66a and 66b. This configuration of the MEMS/device 60 can be used to implement a fluid flow rate sensor, but it can be used as well to measure fluid pressure and/or flow rates.

A fluid source can be attached either to the female connector 51a-52a or 51b-52b for streaming a fluid substance through the MEMS/device 60 and measuring properties of the fluid flowing through the device by the sensor/circuitry elements 66a and/or 66b. For example, and without being limiting, a fluid source (not shown) can be connected to the female connector 51a-52a for introducing a fluid stream into the lumen La, filing the first cavity 63a with the fluid, streaming the fluid through the slender channel 62c into the lumen Lb and filling the second cavity 63b, which in effect introduce a pressure difference between the first and second cavities. The slender channel 62c acts as a flow restrictor, such that as fluid is streamed into the device 60 through the female connector 51a-52a the fluid pressure acting on the portion of the sealing element 66' located over the opening 65a of the first cavity 63a is greater than the fluid pressure acting on the portion of the sealing element 66' located over the opening 65b of the second cavity 63b.

The first and second sensor/circuitry elements 66a and 66b are configured to measure the fluid pressures P1 and P2 in the first and second cavities 63a and 63b, respectively, responsive to deformations of the respective regions of the sealing element 66' covering the first and second opening, 65a and 65b, respectively. Optionally, and in some embodiments preferably, at least one of the first and second sensor/circuitry elements 66a and/or 66b is also configured to determine the pressure difference between the first and second cavities 63a and 63b, and/or the fluid flow rate through the MEMS/device 60, based on the fluid pressures measured in the first and second cavities 63a and 63b.

As will be understood from the following description, the support arms 61d of the MEMS/device 60 are provided to facilitate the production of an array of the MEMS/device 60 in a wafer, and the arm extensions 66d of the sealing element 66' are configured to facilitate attachment of a corresponding array of sealing elements comprising respective array of first and second sensor and/or circuitry elements 66a and 66b, as illustrated in FIG. 6D.

This is needed in this specific embodiment because thickness T of the main body of the MEMS/device 60 is smaller than the outer diameter D of the female connectors 51a-52a and 51b-52b. In this case, the main body of the MEMS/device 60 is thinner than the connectors 51a-52a and 51b-52b, which is convenient for depositing (e.g., metal deposition techniques as, but limited to, evaporation, sputtering, electroplating, electroless plating, or lamination processes combined with lithography processes) the sensor/circuitry elements 66a and 66b on the sealing sheet 66 (e.g., thin foil/film) before the sealing sheet 66 is attached to the assembled arrays A61 and A62. It is noted that in case the thickness of the main bodies of the MEMSs/devices 60 is greater than the outer diameter of the female connectors any suitable fabrication technique can be used i.e., the sensor/circuitry elements 66a and 66b can be deposited before or after attaching the sealing element 66'.

FIG. 6C shows a variant of the fluidic MEMS comprising an upper slender channel 61c configured to fluidly communicate between the first and second openings 65a and 65b. The upper slender channel 61c is sealably closed by the sealing element 66', and it may be provided instead of the bottom slender channel 62c, or in addition to the bottom slender channel 62c.

In FIG. 6D an array of the MEMSs/devices 60 is assembled from an array A61 of the top elongated elements 61 that is attached to a corresponding array A62 of the bottom elongated elements 62, and a corresponding array of sealing elements 66' arranged in a sealing sheet 66. The sealing sheet 66 is configured to sealably cover the first and second openings 65a and 65b, and place respective arrays of first and second sensor/circuitry elements 66a and 66b over them. In this embodiment the sealing sheet 66 is pre-cut to form elongated windows 66w therein at the regions wherein the female connectors 51a-52a and 51b-52b are located.

Figure 6E:
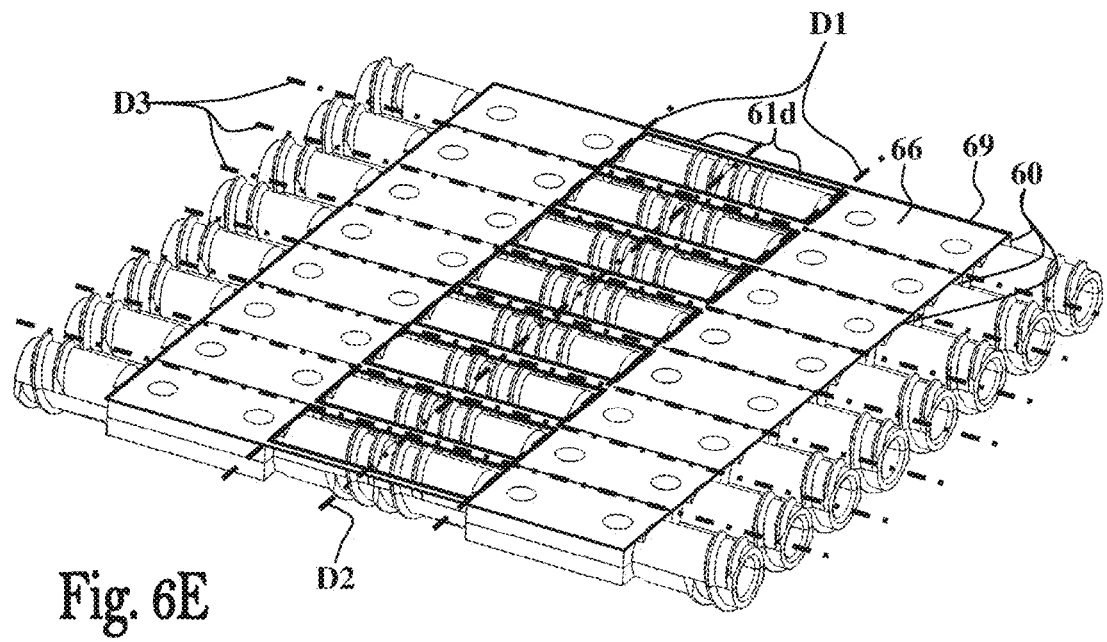

FIG. 6E illustrates a dicing process for cutting the MEMSs/devices 60 out of the wafer 69. The dicing process comprises in some embodiments a preliminary dicing step illustrated by dashed lines D1, in which partial cuts D1 are transversally applied along the top side of the wafer 69 in a relatively short depth sufficient to only cut off the support arms 61d and the arm extensions 66d of the sealing element attached over them. Accordingly, the partial cuts D1 don't pass all the way through the wafer 69, and in some embodiments their depths is in the range of few micrometers to few millimeters. In further dicing steps pass-through cuts are applied, as illustrated by the dashed-dotted lines D2 and D3, to separate the MEMSs/devices 60 from the wafer 69. In these dicing steps one or more traversal pass through cuts D2 are applied to separate the rows of the MEMSs/devices 60 one from the other, and one or more longitudinal pass through cuts D3 are applied to separate the columns of the MEMSs/devices 60 one from the other.

Figure 6F:
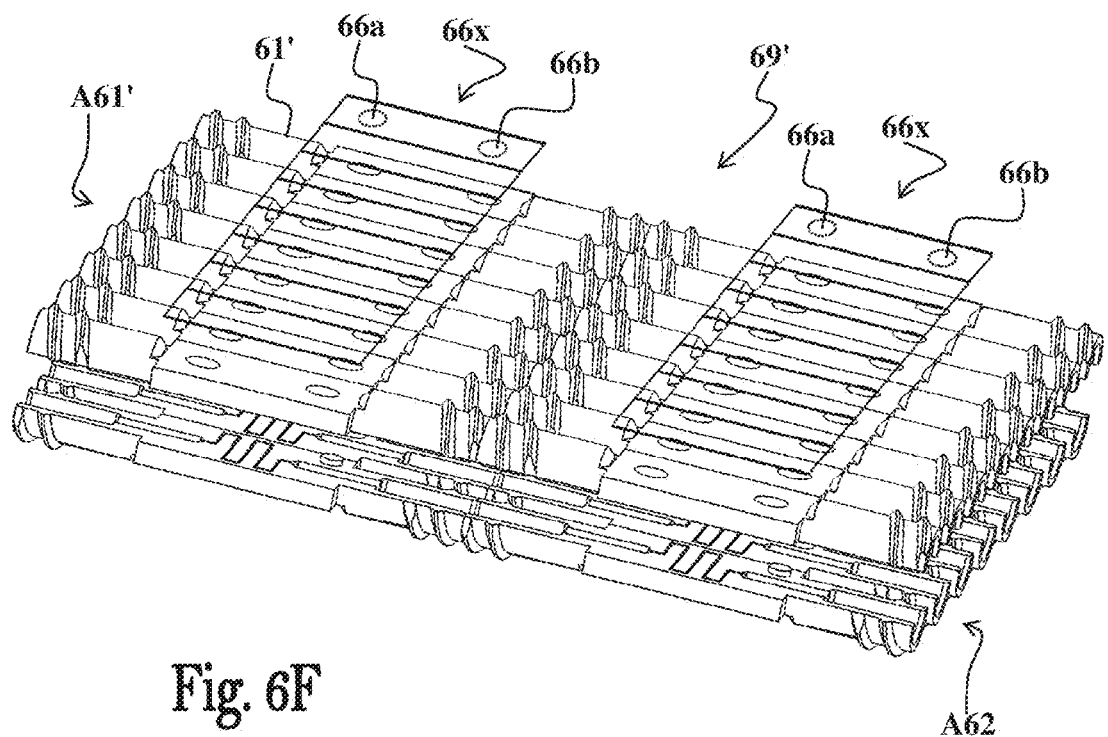

FIG. 6F illustrates a possible embodiment wherein a wafer 69' of the MEMSs/devices 60 is constructed without the support arms 61d. Accordingly, an array A61' of top elongated elements 61', in which there are no support arms 61d, is attached to the array A62 of bottom elongated elements, and separate sealing sheets 66x, each comprising an array of the first and second sensor/circuitry elements 66a and 66b, are then attached over the rows of main bodies of the MEMSs/devices 60 in the array.

As seen and described above, the MEMS/device 60 is assembled from two parts (also referred to herein as body elements) and a sealing element attached over the top openings 63a and 63b, and each one of the different parts 61 and 62 can be easily fabricated by any conventional 3D object production technique without presenting undercuts and/or need to form partially or fully closed cavities.

FIGS. 7A to 7E schematically illustrate structure and construction of a fluidic MEMS/device 70 of some possible embodiments comprising a differential flow sensing element. The structure of the main body of MEMS/device 70 is similar in some aspects to that of MEMS/device 60 of FIGS. 6A to 6F, comprising the elongated bottom element 62 having the same/similar elements, and an elongated top element 61' that is mainly different from elongated top element 61 FIGS. 6A to 6F in having only the first cavity 65b at one side of the slender channel 62c and in having an open fluid passage 73a at the other side of the slender channel 62c. Accordingly, the sealing element 76' attached over the upper surface of the elongated top element 61' has only one sensor and/or circuitry elements 73i patterned/mounted on a surface area thereof located above the opening 63b of the cavity 65b. The sealing element 76' further comprises a pass-through bore 76e configured to provide fluid passage through the fluid passage 73a to the upper side of the sealing element 76'.

The fluidic MEMS/device 70 further comprises a pressure differentiator element 75 (also referred to herein flow transmission body element) configured to form an upper cavity 75c (also referred to herein as fluid transmission passage) over a top region of the sealing element 76' for affecting a fluid pressure thereover from above. The shape of the pressure differentiator 75 substantially complies with the shape of the sealing element 76', and mainly differs in having two lateral indentations 75n configured to provide access to the contact pads (not shown) patterned on the sealing element 76' and in electrical contact with the sensor and/or circuitry elements 73i patterned/mounted over the opening 63b. The pressure differentiator 75 is sealably attached over the sealing element 76' and configured to thereby form an elongated cavity 75c by an open channel formed along a bottom side thereof.

The elongated cavity 75c is configured to receive fluids flowing at one side of the slender channel 62c and affect fluid pressure over the upper side of the portion sealing element 76' covering the opening 63b located at the other side of the slender channel 62c. Due to flow changes affected by the slender channel 62c, two different pressure levels acts over the portion sealing element 76' covering the opening 63b, namely, the fluid pressure P1 in the cavity 65b and the fluid pressure P2 in the elongated cavity 75c. This way, the sensor/circuitry elements 73i placed over the portion of the sealing element covering the opening 63b measures the pressure difference |P1−P2| responsive to deformations thereof.

In some embodiments the elongated cavity progressively transversally tappers towards the opening 63b to reduce the internal volume. Optionally, and in some embodiments preferably, an air ejector hole 75a is formed in the upper side of the pressure differentiator 75 configured for ejecting air/gases trapped inside the elongated cavity 75c. The ejector hole 75a is sealed in some embodiments by a gas permeable membrane 75q. If the MEMS/device 70 is used to measure fluid flow rate, a priming step can be carried out in which the opening of the female connector 51b-52b is temporarily sealably closed and fluid is streamed into the device 70 via the female connector 51a-52a in order to fill the elongated channel 75*c* and eject air/gases therefrom through the permeable membrane 75*q*. Alternatively, the ejector hole 75*a* is sealed in some embodiments after the priming step by sealably attaching thereover a desiccant cap element (not shown), or by a combination of both the permeable membrane 75*q* and the desiccant cap element attached thereover. In some embodiment the MEMS/device 70 can be used for bidirectional flow rate measurements (i.e., the fluid flow can be introduced either via the connector 51*a*-52*a* or the connector 51*b*-52*b*), and in this case the desiccant cap element can be used prevent suction of air via the gas permeable membrane 75*q*.

As shown in FIG. 7D, in this specific and non-limiting example the sealing element 76' can be comprised of at least three different layers, L1, L2 and L3, wherein the topmost layer L1 is a protective/biocompatible layer (film/foil), the intermediate layer L2 comprises the sensor/circuitries 73*i*, and the bottommost layer L3 is a protective/biocompatible layer (foil/film). With this configuration the electrical components of the sensor/circuitries 73*i* in the intermediate layer L2, that are usually not biocompatible, are sealably isolated by the protective/biocompatible layers L1 and L3 sandwiching it, and thereby enable use of MEMS/device 70 with medicinal and/or body fluids (e.g., blood, medicaments, etc.).

Figure 7E:
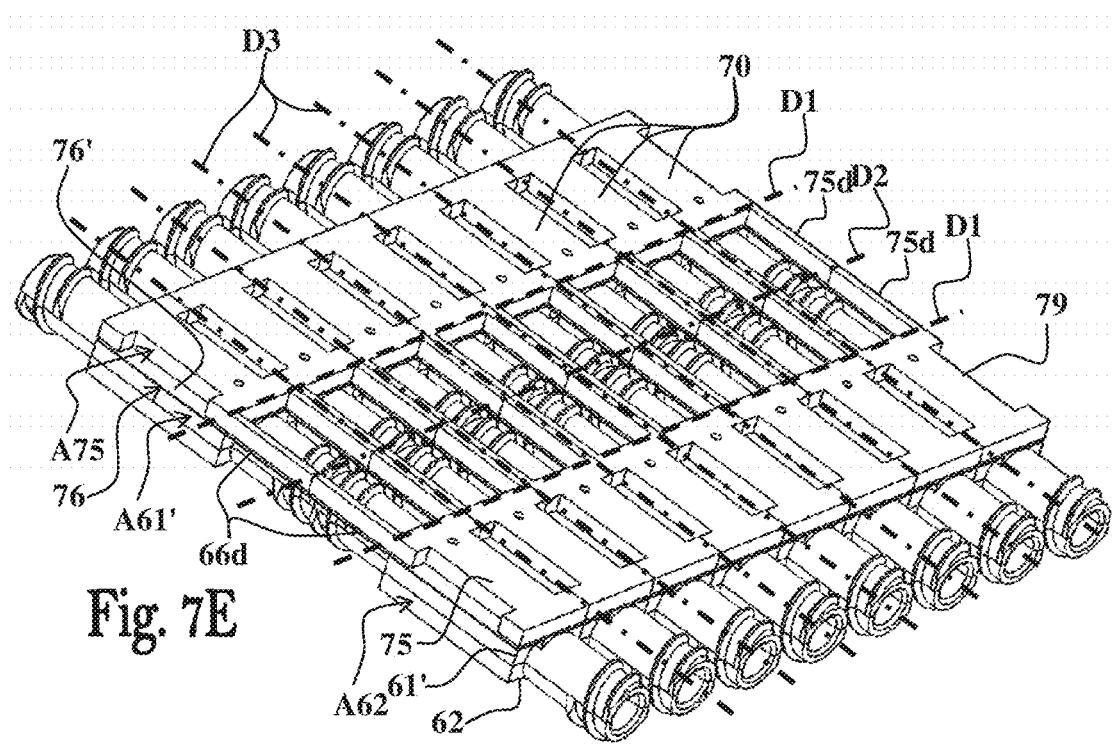

FIG. 7E schematically illustrates construction of an array of the fluidic MEMSs/devices 70 in a form of a wafer 79. This is achieved by fabricating an array A62 of the elongated bottom elements 62, an array A61' of the elongated top elements 61', an array A75 of the pressure differentiator elements 75, and a sealing sheet 76 comprising a respective array of the sealing elements 76'. The wafer 79 is constructed by attaching the array A62 to the array A61' to form the lumens a and b and the connectors 51*a*-52*a* and 51*b*-52*b*, attaching the sealing sheet 76 over the upper surface of the array A61' to seal the openings 63*b* and place the sensor and/or circuitry elements 73*i* thereover while placing the pass-through bores 76*e* over the openings of the open fluid passages 73*a*, and attaching the array A75 over the sealing sheet 76 such that the open channels at the bottom side thereof form the elongated cavities 75*c* for passing fluids from the fluid passages 73*a* to the upper side of the sealing elements 76'.

The dicing of the wafer 79 can comprise several dicing steps, including a preliminary dicing step illustrated by dashed lines D1, in which partial cuts D1 are transversally applied along the top side and the bottom side (not shown) of the wafer 79 in a relatively short depth sufficient to only cut off the support arms 61*d* and portions 66*d* of the sealing sheet attached thereover, and corresponding arms 75*d* of the pressure differentiator element 75. Accordingly, the partial cuts D1 don't pass all the way through the wafer 79, and in some embodiments their depths is in the range of 0.1% to 25% of the wafer thickness. In further dicing steps pass through cuts are then applied, as illustrated by the dashed-dotted lines D2 and D3, to separate the MEMSs/devices 70 from the wafer 79. In these dicing steps one or more traversal pass through cuts D2 are applied to separate the rows of the MEMSs/devices 70 one from the other, and one or more longitudinal pass through cuts D3 are applied to separate the columns of the MEMSs/devices 70 one from the other.

The MEMSs/devices 70 in the wafer 79 can be calibrated using the wafer calibration techniques described hereinabove. In some embodiments the wafer calibration comprises a pressure calibration step performed without the pressure differentiator element 75 by temporarily sealing the pass-through bore 76*e* and the open fluid passage 73*a* therebeneath e.g., by adhesive patch (not shown). The calibration can comprise a flow calibration step performed after removing the temporary seal from the pass-through bore 76*e* and sealably attaching the pressure differentiator element 75 on top of the sealing element 76'.

The MEMS/device 70 is assembled from three body parts/elements and the sealing element 76'. Each one of the different parts 75, 61' and 62, can be easily fabricated by any conventional 3D object production technique without presenting undercuts and/or need to form partially or fully closed cavities.

FIGS. 8A to 8D schematically illustrate structure and construction of a fluidic MEMS/device 80 comprising a conductivity sensor unit 88 patterned or mounted on its sealing element 66". The elongated top and bottom elements 61" and 62" of the MEMS/device 80 have shape and structure similar to those of the elongated top and bottom elements 61 and 62 of FIGS. 6A and 6B, and its shielding element 75" have shape and structure similar to those of the pressure differentiator element 75 of FIGS. 7A to 7C. The main differences are that the base section 62*s*" of the elongated bottom element 62" comprises a partition 62*p* between its first and second open channels, 62*a* and 62*b* (i.e., without the slender wavy channel 62*c*), the elongated top element 61" comprises an open upper channel 73*e* communicating with the first open channel 61*a* via passage 73*a* and with the second open channel 61*b* at its other side via the passage 73*b*, and that the shielding element 75" is a full and solid element (i.e., not including fluid channels or opening).

Accordingly, when the elongated top and bottom elements 61" and 62" respectively are attached one to the other they form the female connectors 51*a*-52*a* and 51*b*-52*b*, and the respective lumens a and b communicating between the connectors 51*a*-52*a* and 51*b*-52*b* and the open upper channel 73*e* of the top elongated element 61". The open upper channel 73*e* is sealed by the sealing element 66", which thereby forms a continuous fluid passage 80*c* along the length of the MEMS/device 80, starting from connector 51*a*-52*a* through lumen a and fluid passage 73*a* into the upper channel 73*e*, and therefrom through the fluid passage 73*b* and the lumen b to the connector 51*b*-52*b* (or the other way around). The sealing element 66" is similar in shape to the sealing element 66' of FIG. 6A, and therefore will not be described in details. The shielding element 75" is then attached over the sealing element 66" to substantially immobilize and prevent deformations of the portion of the sealing element 66" located over the open upper channel 73*e* of the top elongated element 61" when pressure forces are applied thereon by fluids flowing through the channel 73*e*, and to provide thermal insulation from the external environment.

Figure 8A:
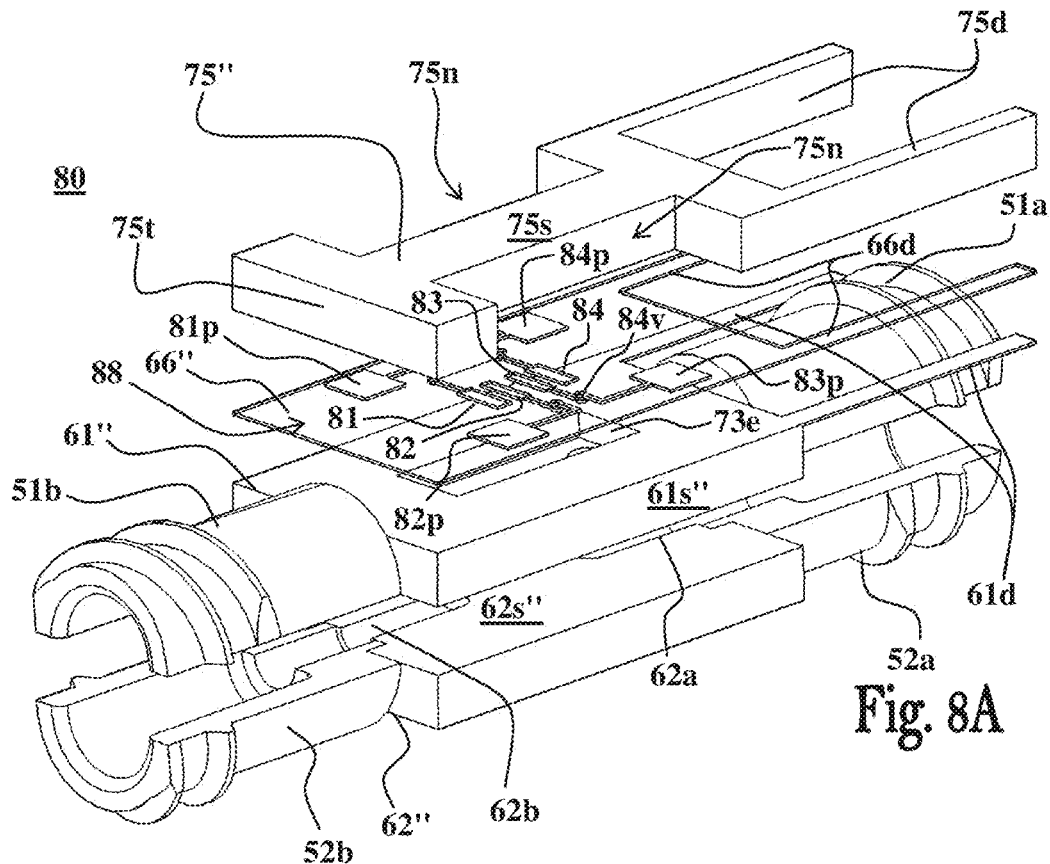
Figure 8B:
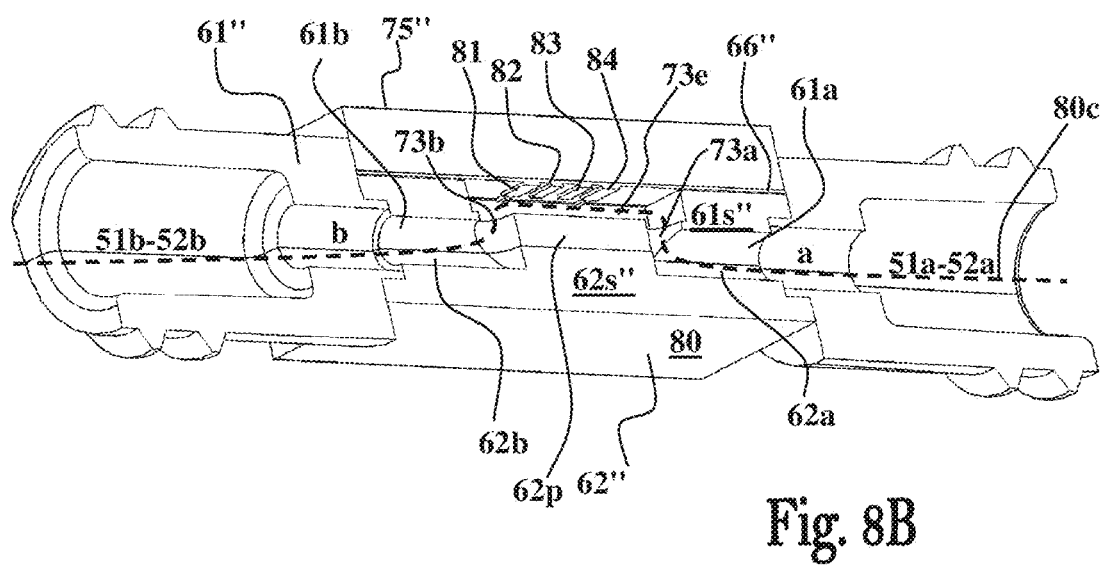
Figure 8C:
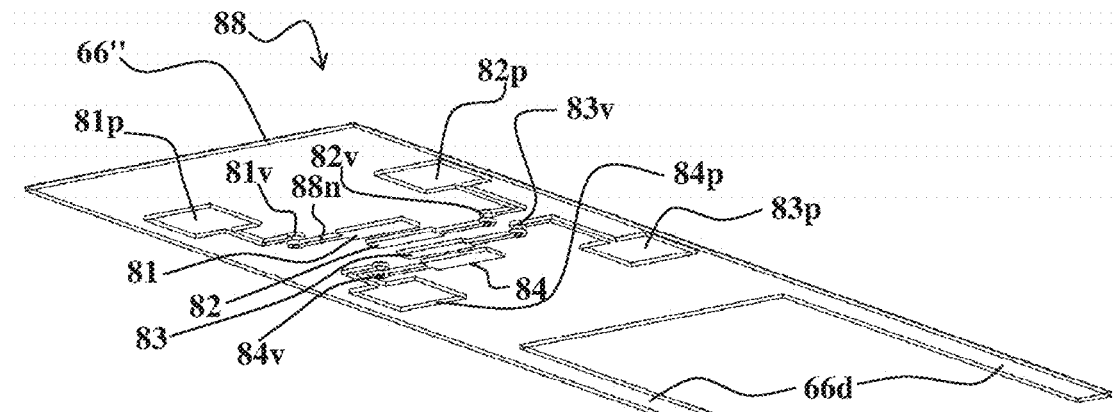

With reference to FIG. 8C, the conductivity sensor unit 88 comprises electrically conducting patterns formed on the upper and bottom sides of the sealing element 66". The upper side of the sealing element 66" comprises four contact pads, 81*p* and 84*p* located at one lateral side of the sealing element 66", and 82*p* and 83*p* located at the other lateral side of the sealing element 66". Four electrodes 81, 82, 83 and 84, are patterned or mounted on the bottom side of the sealing element 66", each electrically coupled with a respective one of the contact pads via a respective via and conducting lines 88*n*. More particularly, the bottom side electrode 81 is electrically connected to the upper side contact pad 81*p* through the via 81*v*, the bottom side electrode 82 is electrically connected to the upper side contact pad 82*p* through the via 82*v*, the bottom side electrode 83 is electrically connected to the upper side contact pad 83p through the via 83v, the bottom side electrode 84 is electrically connected to the upper side contact pad 84p through the via 84v.

In this specific and non-limiting example the electrodes 81, 82, 83 and 84, are aligned in a row on the bottom side of the sealing element 66", such they become aligned along the upper channel 73e after the sealing elements 66" is attached to the elongated top element 61". This configuration thus provides a four point measurement setup when a fluid substance is streamed through the channel 80c and the electrode 81, 82, 83 and 84, are in contact with the streamed fluid.

The contact pads 81p, 82p, 83p and 84p, electrodes 81, 82, 83 and 84, and the electrically conducting lines 88n, can be made from gold, platinum, titanium patterned on the sealing element 66", which can be alternatively made of by any nonconductive polymer (e.g., polycarbonate, peek, polyimide, etc.). The same materials and processes can be used in fabrication of the electrical/sensor elements in the various different sealing and/or deformable elements of the other embodiments disclosed herein. After assembling together the various elements of the MEMS/device 80 its contact pads 81p, 82p, 83p and 84p, can be accessed and electrically contacted via the lateral indentations 75n formed in the lateral sides of the shielding element 75".

Figure 8D:
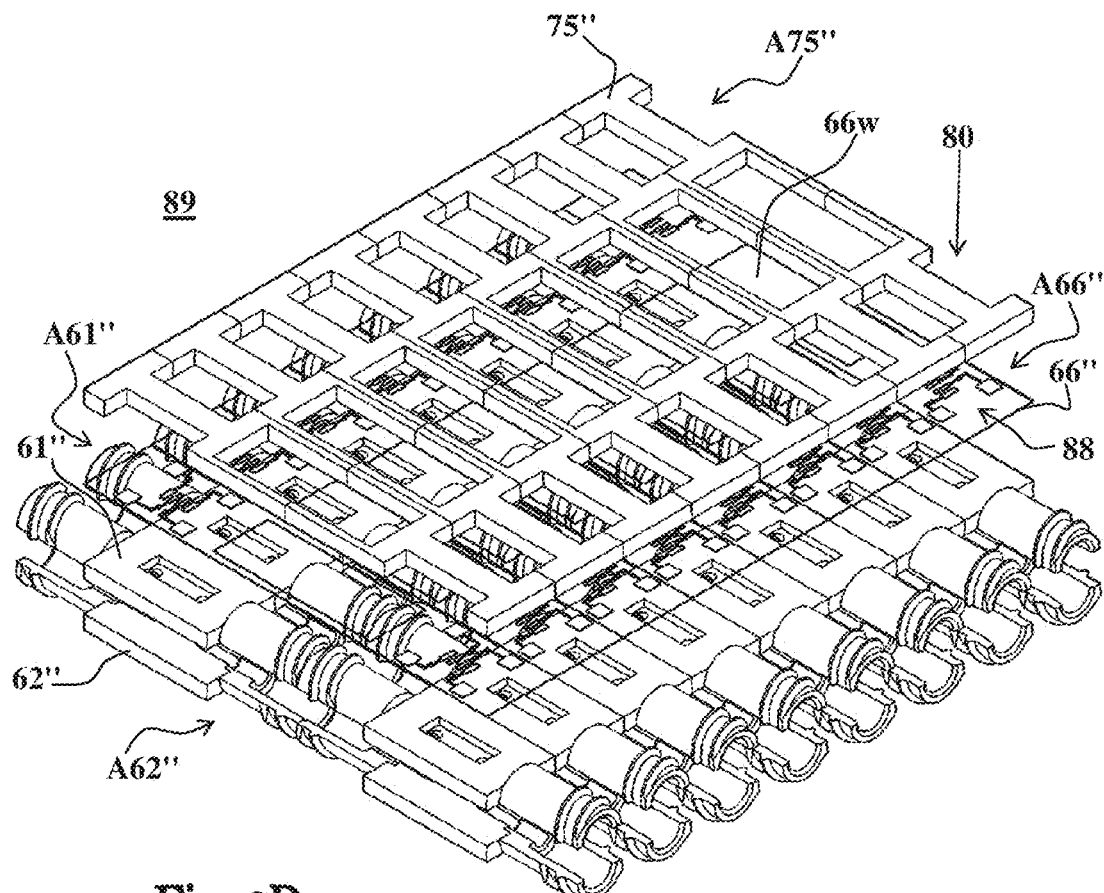
Figure 8E:
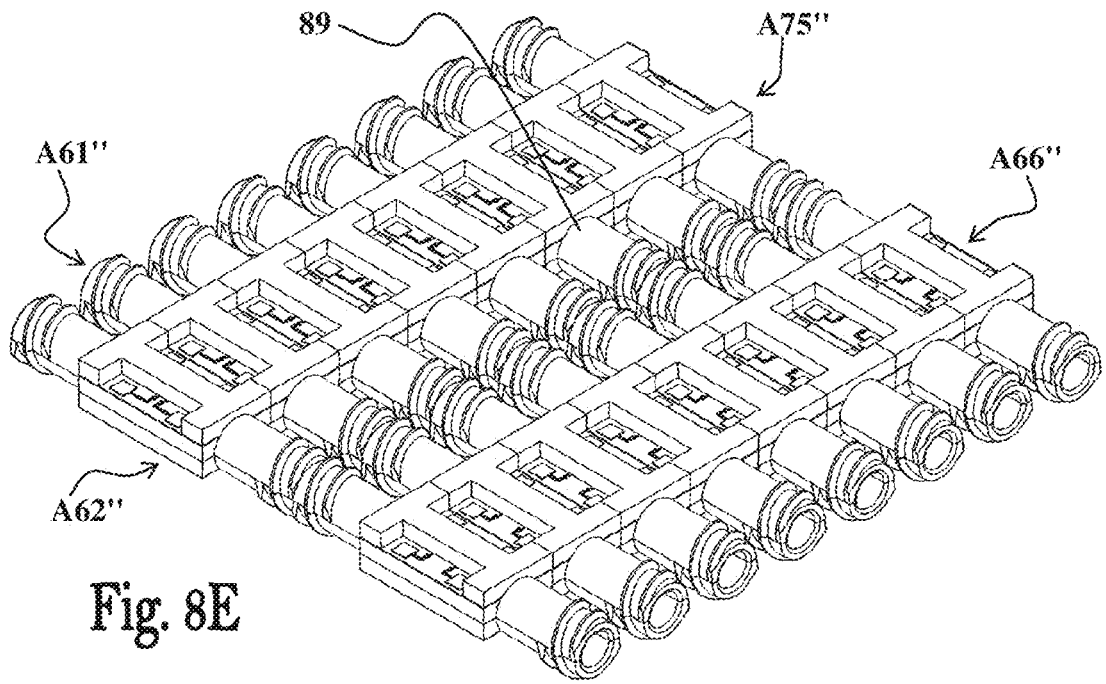

FIGS. 8D and 8E schematically illustrates construction of an array of MEMSs/devices 80 in a layered fashion to form a multilayered wafer 89 of the MEMSs/devices 80. The wafer 89 is constructed from an array A62" of a plurality of elongated bottom elements 62" aligned in rows and columns attached to a respective array A61" of a plurality of elongated top element 61". A respective array of sealing elements 66" is attached in a form of a sealing sheet A66" similar in shape to the sealing sheet 66 of FIGS. 6D and 6E i.e., comprising the support arms 61d and the elongated windows 66w, but further comprising a respective array of the conductivity sensor unit 88 patterned or mounted on its bottom and upper sides, as described hereinabove and shown in FIG. 8C, for sealing the open upper channels 73e of the elongated top elements 61" and placing the electrodes 81, 82, 83 and 84, of each sensor unit 88 aligned therealong. A respective array A75" of the shielding elements 75" is attached over the sealing sheet A66" to immobilize and thermally isolate the portions of the sealing sheet A66" covering the open upper channels 73e and carrying the electrodes 81, 82, 83 and 84.

FIGS. 9A to 9D schematically illustrate structures and constructions of fluidic MEMSs/devices 90, 90' and 90", of some possible embodiments, comprising several different sensing elements. The MEMS/device 90 in FIGS. 9A and 9B generally comprises elongated top and bottom elements, 91 and 92 respectively, configured to attached one to the other and form a fluid passage 98 of the MEMS/device 90, a sealing element 96 configured to sealably attach to the upper surface of elongated top element 91 over openings/channels thereof and place electrical/sensing elements thereover, and a shielding element 97 configured to attach over the sealing element 96, immobilize and/or thermally isolate the portions of the sealing elements placed over the openings/channels and carrying the electrical/sensing elements of the MEMS/device 90.

The bottom elongated element 92 comprises at its extremities female connector portions 52a and 52b, and a first open channel 62a extending from the connector portion 52a, and a second open channel 62b extending from the connector portion 52b, as described and shown in FIGS. 6A-B, 7A-B and 8A-B. The bottom elongated element 92 also comprises an intermediate open channel 62k passing along a length about the center of the base portion 92s of the bottom elongated element 92. A first partition portion 62g formed in the base portion 92s of the bottom elongated element 92 partitions between the first open channel 62a and the intermediate open channel 62k, and a second partition member 62f formed in the base portion 92s partitions between the second open channel 62b and the intermediate open channel 62k.

The elongated top element 91 comprises at its extremities female connector portions 51a and 51b, and a first open channel 61a extending from the connector portion 51a, and a second open channel 61b extending from the connector portion 51b, as described and shown in FIGS. 6A-B, 7A-B and 8A-B. The top elongated element 91 also comprises an upper open channel 91c extending from one end along a length of the base portion 91s thereof and overlapping an end portion of the second open channel 61b, a bottom intermediate channel 61k extending along a length of base portion 91s and overlapping with an end portion of the upper open channel 91c, and an upper open cavity 91d near another end of the base portion 91s overlapping with an end portion of the bottom intermediate channel 61k at one side thereof and overlapping with an end portion of the first open channel 61a at another side thereof.

The base portion 91s of the elongated top element 91 comprises a first partition portion 61g partitioning between the first open channel 61a and the bottom intermediate channel 61k, an intermediate partition portion 91k partitioning between the upper open channel 91c and the upper open cavity 91d, and a second partition portion 61f partitioning between the second open channel 61b and the bottom intermediate channel 61k. A fluid passage 61w formed in the base portion 91s communicates between the first open channel 61a and the upper open cavity 91d, a fluid passage 61z communicates between the upper open cavity 91d and the bottom intermediate channel 61k, a fluid passage 61y communicates between bottom intermediate channel 61k and the upper open channel 91c, and a fluid passage 61x communicates between upper open channel 91c and the second open channel 61b.

When the elongated bottom element 92 is attached to the elongated top element 91 the connector portions 51a and 52a are joint to form a connector 51a-52a and their threading portions are joined to form a complete threading structure, and the connector portions 51b and 52b are joint to form a connector 51b-52b and their threading portions are joined to form a complete threading structure. In this assembled state the first open channels 61a and 62a are joint to form the first lumen a, the second open channels 61b and 62b are joint to form the second lumen b, and the intermediate channels 61k and 62k are joined to form the intermediate lumen k. Also, the first partition portions 61g and 62g are joined to form a partition 61g-62g between the first lumen a and the intermediate lumen k, and the second partition portions 61f and 62f are joined to form a partition 61f-62f between the second lumen b and the intermediate lumen k.

The sealing element 96 is attached over the an upper surface of the base portion 91s of the top elongated element 91 to seal the upper open cavity 91d and place thereover a first sensing unit 96d, and to seal the upper open channel 91c and place thereover a second sensing unit 96c. This way a fluid channel 98 is formed along the MEMS/device 90, passing from the connector 51a-52a to the first lumen a, from the first lumen a through the fluid passage 61w into the upper open cavity 91d and therefrom through the fluid passage 61z into the intermediate lumen k, from the intermediate lumen k through the fluid passage 61y into the upper open channel 91c and therefrom through the fluid passage 61x into the second lumen b and to the connector 51b-52b.

The shielding element 97 is attached over the sealing element 96 to immobilize and thermally isolate the portion of the sealing element covering the upper open channel 91c and carrying the second sensing unit 96c. The shielding element 97 comprises a bottom open cavity 97d configured to form a closed cavity 91d-97d when attached over the sealing element 96 for allowing deformations of the portion of the sealing element 96 enclosed therewithin and thermally and physically isolating it from the external environment. The shielding element 97 is generally a "H"-shaped element having two lateral support elements 97a and 97b and an intermediate section 97c extending between them, thereby forming two lateral indentations 97n that provide access to contact pads (not shown) of the first and second sensor units 96d and 96c formed/mounted on lateral portions of the sealing element 96. The intermediate section 97c can comprise a disk shaped portion 97u configured to accommodate the bottom open cavity 97d.

The first sensor unit 96d can thus be a type of tension sensor configured to measure pressure and/or flow rate of fluid passing through the upper open cavity 91d and causing deformations of the portion of the sealing element 96 located thereon in (or out) of the bottom open cavity 97d of the shielding element 97. In this embodiment the portion of the sealing element 96 covering the upper open cavity 91d is sealed from the external environment. In some embodiments the sealing created by the bottom open cavity 97d is configured to maintain a specific predefined pressure level inside the cavity 97d and thereby implement by the first sensor unit 96d an absolute pressure sensor. The second sensor unit 96c can comprise a temperature sensor, such as, but not limited to, the temperature sensor 41e of FIG. 4A, and/or a type of sensor configured to contact the fluid in the upper open channel 91c, such as, but not limited to, the conductivity sensor 88 of FIG. 8c.

Figure 9A:
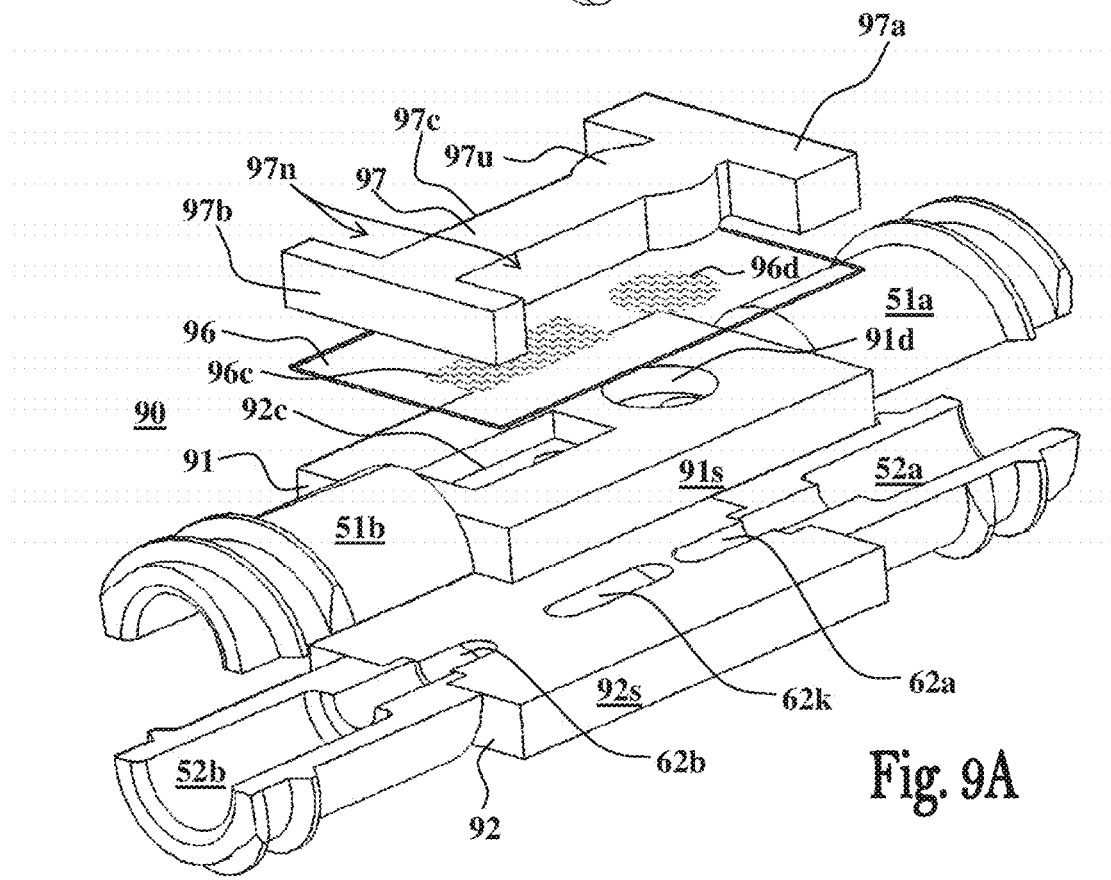
Figure 9B:
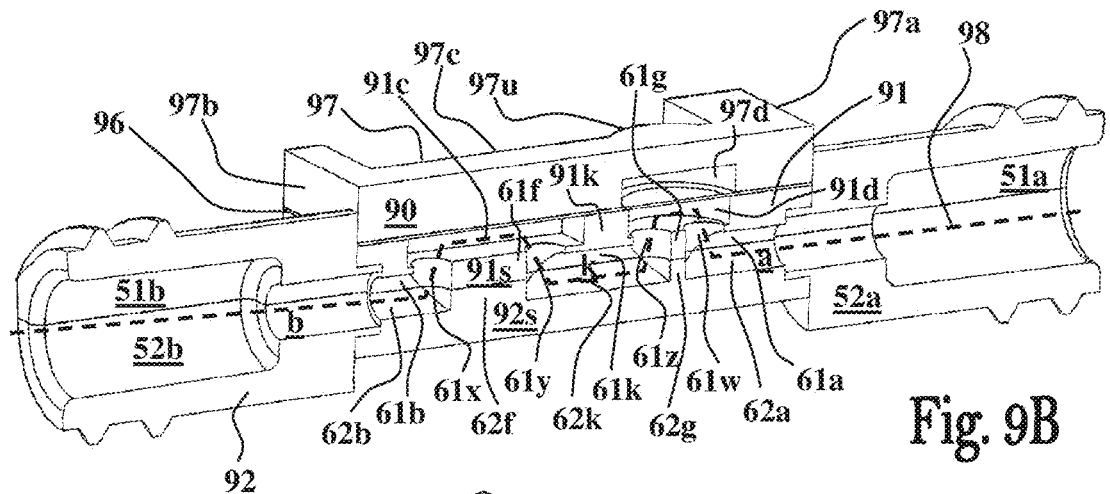
Figure 9C:
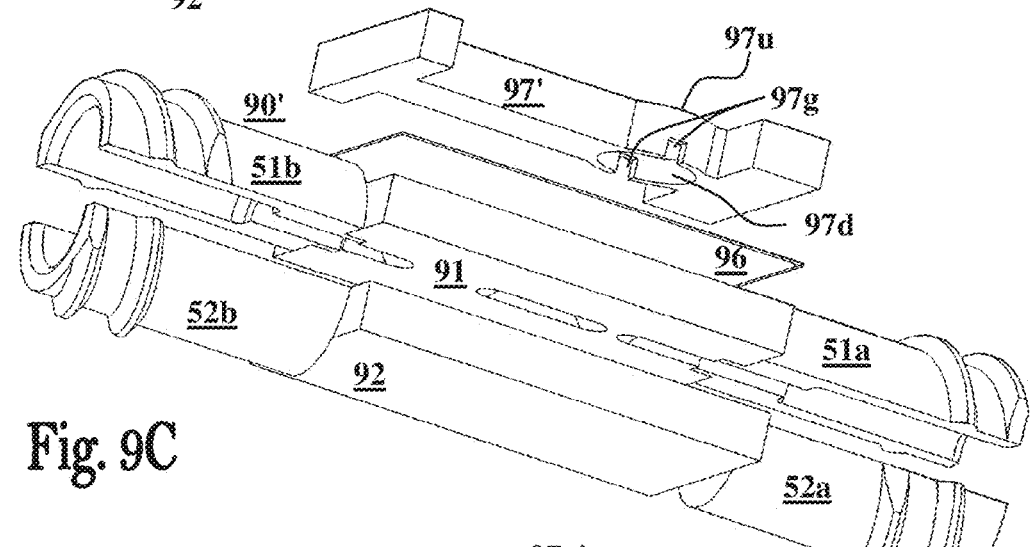
Figure 9D:
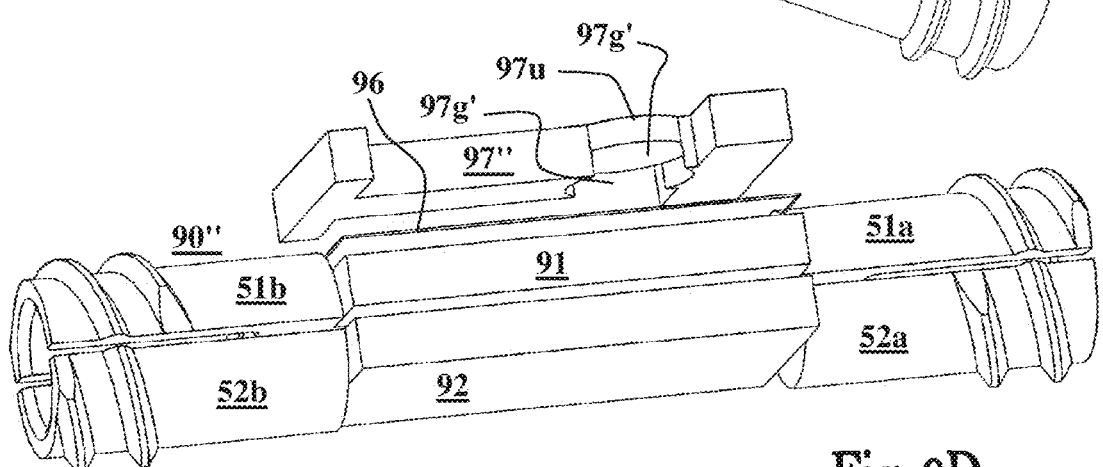

FIGS. 9C and 9D schematically illustrate variants 90' and 90" respectively, of the MEMS/device 90 wherein the portion of the sealing element 96 covering the upper open cavity 91d is exposed to environmental pressure. In FIG. 9C the disk shaped portion 97u of the shielding element 97 comprises two or more lateral openings 97g configured to allow air flow from the external environment into the cavity 97d. In FIG. 9D the disk shaped portion 97u of the shielding element 97 is a thin disk element forming two lateral air passages 97g' such that no cavity 97d is formed, and air can freely flow from the external environment therethrough. In some embodiments the first sensor unit 96d of MEMSs/devices 90' and 90" is configured to implement a gauge pressure sensor.

It is noted that though the air passages 97g' in this specific embodiment are formed on the sides of the disk shaped portion 97u, they can be also implemented on the top surface are of the disk shaped portion 97u. Accordingly, in this embodiment there is no cavity that can maintain a specific pressure over the sealing element portion covering the upper open cavity 91d, such that the upper side of the sealing element covering the upper open cavity 91d is subject to the atmospheric pressure at all times i.e., it cannot implement an absolute pressure sensor.

The configurations illustrated in FIGS. 9B and 9C advantageously: (i) protect the first sensing unit 96d, which can a be a delicate and sensitive elements, from the external contact (e.g., of the user hands/fingers when handling the sensor); add mechanical force at the sides of the sealing element and thereby prevent detachment thereof; and/or (iii) in the configuration shown in FIG. 9B, implement an absolute pressure sensor.

The larger air passages 97g' provided in FIG. 9D are configured to reside relatively distant from the edges of the sealing element. In this configuration the assembly process of the MEMS/device 90' is simplified since it does not require accurate alignment of the shielding element 97 with the elongated top element 91 located therebeneath. There is no need to precisely align the shielding element 97 with the edges of the portion of the sealing element covering the upper open cavity 91d, since at worse case misalignment of the shielding element 97 can affect the performance of the sensor and the repeatability among different sensors.

Figure 9E:
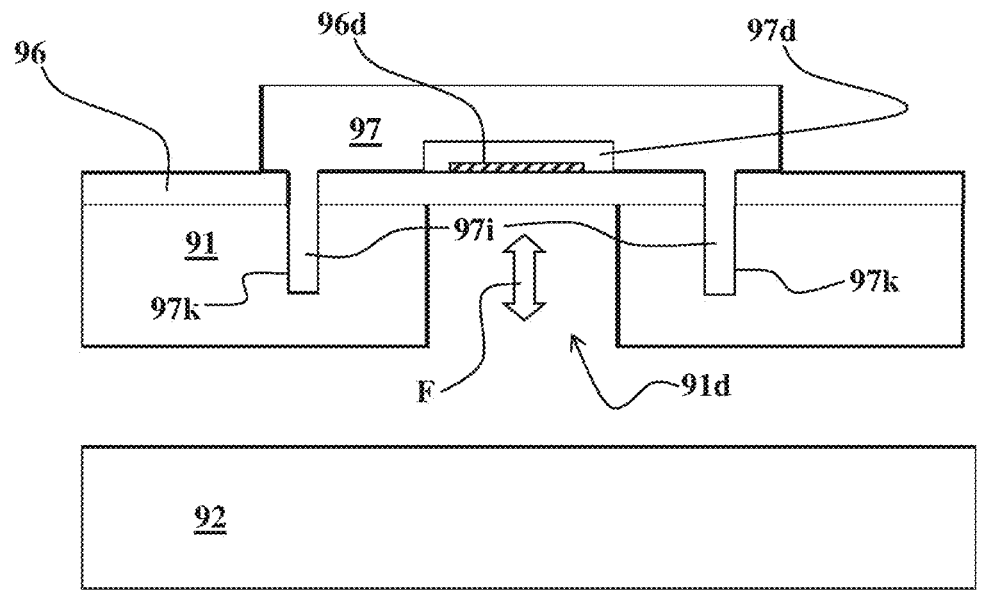

FIG. 9E is a sectional view schematically illustrating attachment of the shielding element 97 to the bottom elongated element 92 by attachment pins or plugs 97i. In the configuration of FIG. 9E the first sensing unit 96d provided on the sealing element 96 is enclosed by the open cavity 97d in the shielding element 97, thereby allowing free movement/deformations of the portion of sealing element placed over the upper open cavity 91d, and can press the membrane edges to avoid detachment thereof. The attachment pins 97i can have sharp ends configured to penetrate into the body of the bottom elongated element 92 to obtain firm attachment thereto, or alternatively, they can be configured to be received in respective fitting sockets 97k. The attachment pins or plugs 97i of the shielding element 97 can be bonded, glued, and/or snapped inside, or around lateral edges of, the base elements. This configuration improves the mechanical robustness and helps to prevent detachment of the sealing element 96 on which the shielding element 97 is attached about the lateral edges. In some embodiments the shielding element 97 is prepared without the open cavity 97d e.g., when the first sensing unit 96d does not require deformations of the sealing element 96 for the measurements.

Optionally, the shielding element 97 comprises one or more pass-through holes configured to allow flow of air to the surface area of the sealing sheet 96 comprising the electrical/sensing elements, to form an open (unsealed) chamber thereabout.

The MEMS/device 90, 90' and 90", are assembled from three body parts/elements and a sealing element 96, and each one of the different body elements 97/97'/97", 91 and 92 can be easily fabricated by any conventional 3D object production technique without presenting undercuts and/or need to form partially or fully closed cavities.

It is noted that the shielding elements used in MEMS embodiments disclosed herein advantageously also prevent detachment of the sealing element on which it is attached at the edges. In some embodiments the shielding element can be of smaller dimensions than the sealing element, and it can be implemented mutatis mutandis in all of the embodiments disclosed herein.

Figure 10A:
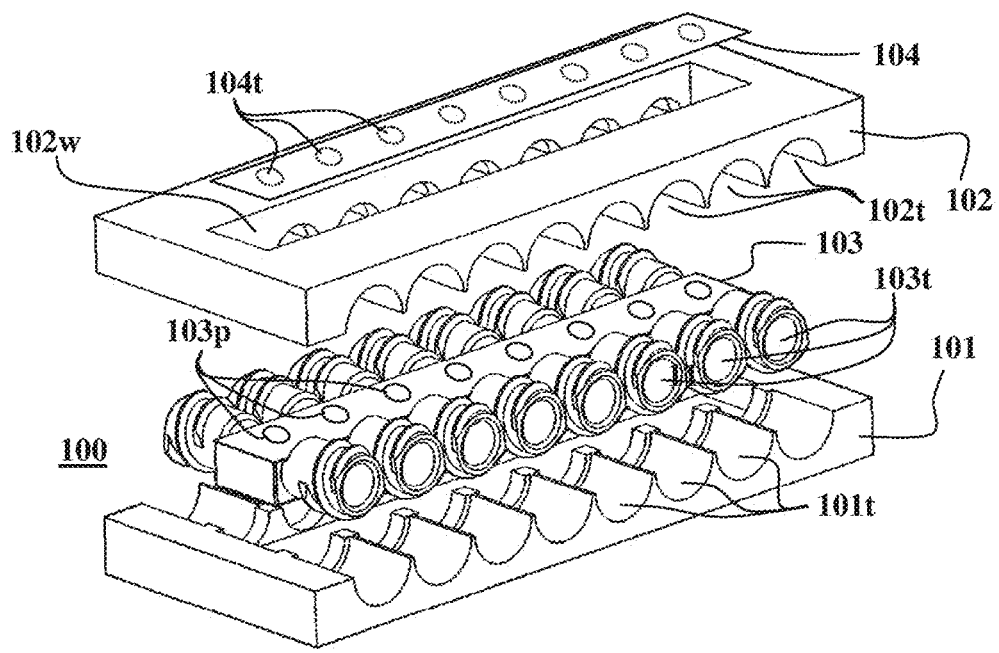
Figure 10B:
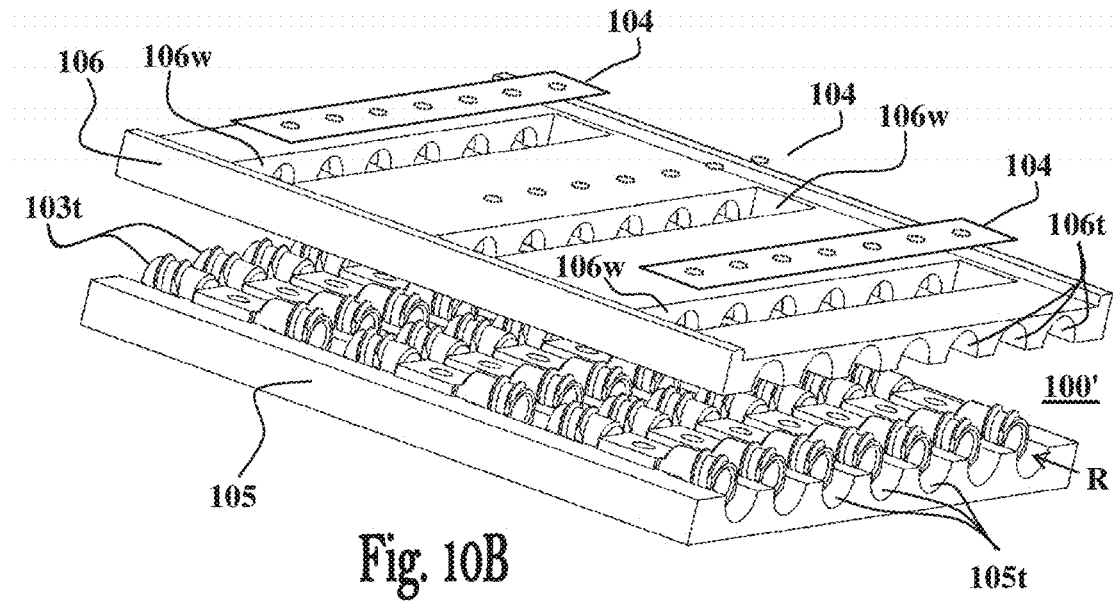
Figure 10C:
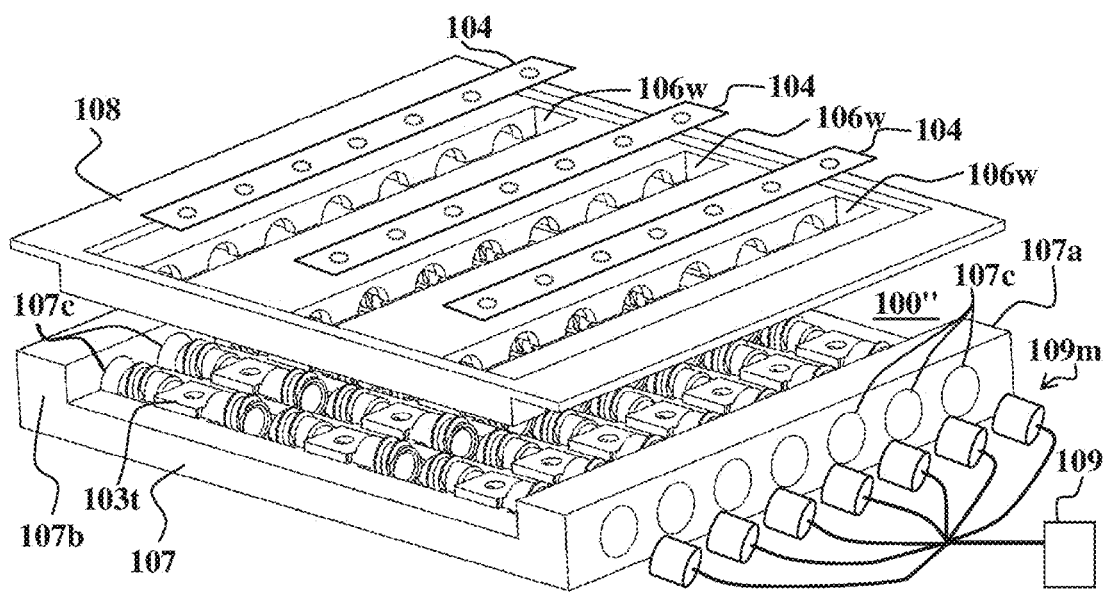

FIGS. 10A to 10C schematically illustrate arrangements configured for holding an array of fluidic MEMSs, for attachment of sealing elements thereon and/or for conducting wafer level calibration. FIG. 10A shows a perspective view of an arrangement 100 for holding a wafer including a single row 103 of MEMSs/devices 103t. The arrangement 100 comprises a holder structure 101 comprising an array of sockets 101t, each configured to snugly receive, hold and immobilize a respective MEMS/device 103t of the array 103. In this specific and non-limiting example the holder structure 101 is configured to hold a single row of MEMSs/devices 103t. The array 103 can be in a pre-diced wafer form wherein the MEMSs/devices 103*t* are integrally connected one to the other as a multilayered structure.

Alternatively, the array 103 can be an array of discrete mechanically separate MEMSs/devices 103*t*, each of which is separately located in a respective socket 101*t* of the holder structure 101 i.e., the MEMSs/devices 103*t* are manufactured as separated units and then placed in holder 101. The sockets 101*t* of the holder 101 are located one adjacent the other such that the MEMSs/devices 103*t* placed in them form a wafer/array 103.

After placing each MEMS/device 103*t* in a respective socket 101*t* a sealing sheet 104 comprising a respective array of electric/sensor elements 104*t* can be placed over the array 103 such that each of electric/sensor elements 104*t* thereof is precisely placed over an opening 103*p* in the respective MEMS/device 103*t*. In some embodiments a holding frame 102 is placed on the holder structure 101 over the array 103 to further stabilize and immobilize the MEMSs/devices 103*t*. The holding frame 102 comprises a respective array of sockets 102*t*, each configured to snugly fit over a respective MEMS/device 103*t* of the array 103, and an elongated window 102*w* configured to provide access to the upper surfaces if the base bodies of the MEMSs/devices 103*t* of the array 103 for facilitating accurate placement of the sealing sheet 104 thereon.

Optionally, after placing each MEMS/device 103*t* in a respective socket 101*t* a sealing element comprising an electric/sensor elements 104*t* is discretely attached separately to each MEMS/device 103*t*.

The holder arrangement 100 can be advantageously used to conduct wafer level calibration for simultaneously calibrating all of the MEMSs/devices 103*t* of the array 103 under the same calibration conditions and measuring the same by their electric/sensor elements 104*t*.

FIG. 10B shows a holder arrangement 100' comprising a holder structure 105 comprising an array of sockets 105*t*, each configured to snugly receive, hold and immobilize a respective discrete separately fabricated MEMS/device 103*t*. The sockets 105*t* are arranged such that after placing the MEMSs/devices 103*t* in them a wafer of the MEMSs/devices 103*t* is practically obtained. A support frame 106 comprising a respective array of sockets 106*t*, each configured to snugly fit over a respective one of the MEMSs/devices 103*t*, hold and immobilize it in place, can be used to further stabilize the array structure. The support frame 106 can be further configured to sealably communicate between the fluid channels of the MEMSs/devices 103*t* in each row R and thereby obtain fluidic continuity between the MEMSs/devices 103*t* in each row R, to thereby facilitate wafer level calibration of at least one row the MEMSs/devices 103*t* per calibration step.

After placing the MEMSs/devices 103*t* in respective sockets of the holder 105 and placing the support frame 106 thereover, sealing sheets 104 can be accurately attached thereon via the elongated windows 106*w* of the support frame 106. Optionally, and in some embodiment preferably the holder structure 105 comprises an array of protuberance (not shown) provide a flat surface between the top surfaces of each pair of locally adjacent MEMSs/devices 103*t*, to thereby facilitate the attachment of the sealing sheets 104 thereover, as a continuous flat surface is thereby obtained.

FIG. 10C shows a holder arrangement 100" comprising a holder structure 107 comprising an array of sockets, each configured to snugly receive, hold and immobilize a respective discrete separately fabricated MEMS/device 103*t*. A support frame 108 comprising a respective array of sockets, each configured to snugly fit over a respective one of the MEMSs/devices 103*t*, hold and immobilize it in place, is also provided. The support frame 108 is further configured to sealably communicate between the fluid channels of the MEMSs/devices 103*t* in each row and thereby obtain fluidic continuity between the MEMSs/devices 103*t* in each row, to thereby facilitate wafer level calibration of at least one row the MEMSs/devices 103*t* per calibration step.

The holder structure 107 comprising front and back panels 107*a* and 107*b*, each comprising a set of connectors 107*c*, each being in fluid communication with one of the rows of the MEMSs/devices 103*t*. The arrangement 100" is adapted to facilitate wafer level pressure calibration by connecting a fluid source 109 to the plurality of rows of MEMSs/devices 103*t* via a manifold of fluid connectors 109*m*, thereby allowing to concurrently apply the same conditions to all of the MEMSs/devices 103*t* in each row. This way wafer lever pressure calibration can be conducted without directly connecting a fluid source to the to the connector of the MEMSs/devices 103*t*. It is noted that for flow rate calibration the manifold 109*m* is not necessary since there is no reliable way to determine the exact flow rate through each of MEMSs/devices 103*t* in each row R.

Figure 11A:
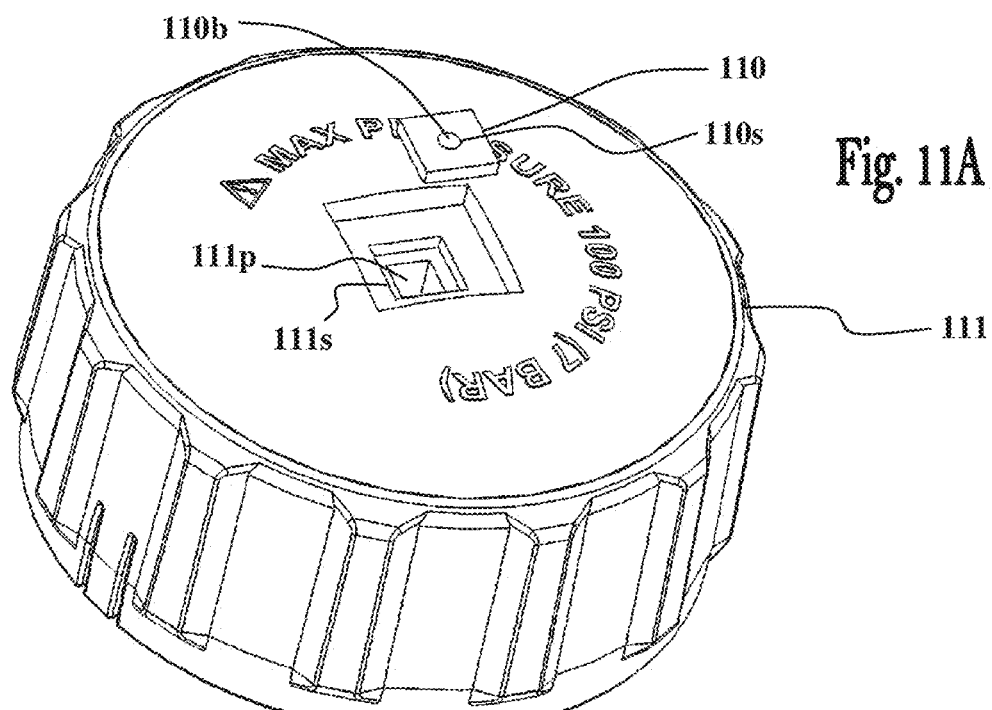
Figure 11B:
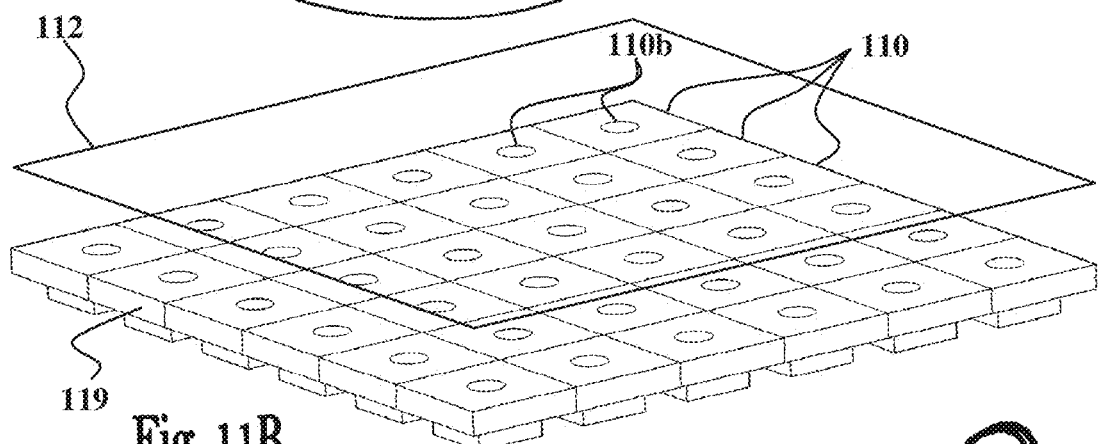
Figure 11C:
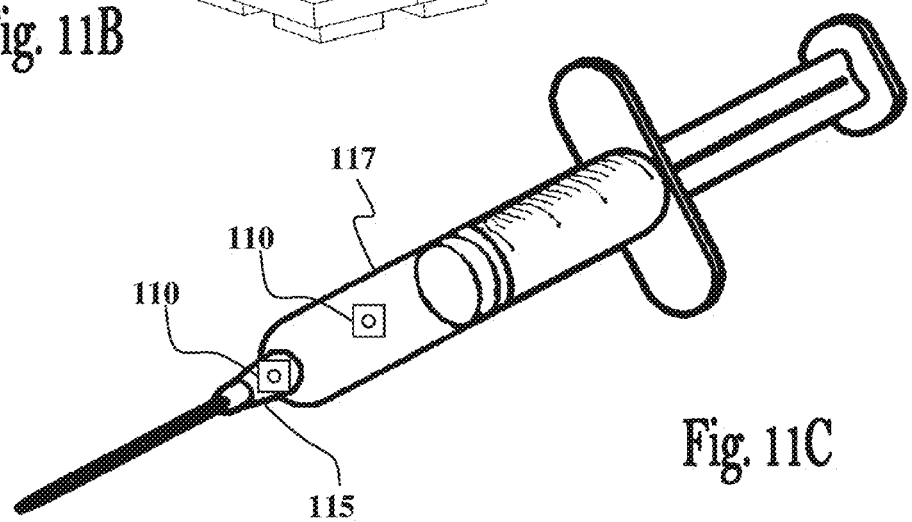

FIGS. 11A to 11C schematically illustrate fluidic MEMS/device 110 of some possible embodiments implemented without fluidic channel(s). FIG. 11A shows an application of the fluidic MEMS/device for a sealing object 111 (e.g., container/bottle cup). The MEMS/device 110 comprises a pass through bore 110*b* and a sealing element 110*s* sealably attached over the bore 110*b*, and comprising one or more electrical/sensor elements patterned/mounted thereon (not shown). The sealing object 111 comprises a pass through bore 111*p* for communicating with the interior of a container (not shown) of the sealing object 111, and a socket 111*s* formed about the pass through bore 111*p* for sealably attaching the MEMS/device 110 thereover for measuring pressure condition in the container of the sealing object 111.

FIG. 11B shows fabrication of an array 119 of the fluidic MEMSs 110. The array 119 comprises a plurality of rows and columns of the fluidic MEMSs 110 forming a wafer having a substantially flat upper surface on which a sealing sheet 112 comprising a respective array of electrical/sensor elements (not shown) is attached for precisely placing them over respecting pass through bores of the MEMSs 110.

FIG. 11C demonstrates applications of the fluidic MEMS 110 in a syringe hub 115 and/or in a syringe barrel 117.

The thickness of the sealing sheet/element in some embodiments is in the range of 0.1 to 2000 micrometer, optionally between 10 to 200 micrometer. In possible embodiments at least some of the electrical contacts/patterns, and/or the additional circuitries, and/or the electrical conducting lines, and/or the sensing elements, and/or actuating means, are mounted/deposited on the sealing sheet/element before it is attached to the wafer.

Terms such as top, bottom, front, back, right, and left and similar adjectives in relation to orientation of the MEMSs/device and their components refer to the manner in which the illustrations are positioned on the paper, not as any limitation to the orientations in which the apparatus can be used in actual applications. It should also be understood that throughout this disclosure, where a process or method is shown or described, the steps of the method may be performed in any order or simultaneously, unless it is clear from the context that one step depends on another being performed first.

As described hereinabove and shown in the associated figures, the present disclosure provides structures and construction techniques of fluidic MEMSs/device configured to measure properties and/or conditions of a fluidic substance. While particular embodiments of the invention have been described, it will be understood, however, that the invention is not limited thereto, since modifications may be made by those skilled in the art, particularly in light of the foregoing teachings. As will be appreciated by the skilled person, the invention can be carried out in a great variety of ways, employing more than one technique from those described above, all without exceeding the scope of the claims.

The invention claimed is:

1. A fluidic sensor device comprising:
a base body structure comprising a fluid channel or cavity passing therealong and at least one opening in an external face of said base body structure and being in fluid communication with said fluid channel or cavity; and
a sealing element comprising a deformable portion and one or more sensing elements a priori patterned thereon, wherein
said sealing element is sealably attached over said external face of said base body structure comprising said at least one opening such that the one or more sensing elements a priori patterned thereon become located over said at least one opening,
said one or more sensing elements are configured to measure at least one property or condition of a fluid substance responsive to deformations of said deformable portion when said fluid substance is introduced into said fluid channel or cavity and interact with said sealing element located over said at least one opening, and
at least said deformable portion of said sealing element is a multilayered structure having an inner layer comprising the one or more sensing elements a priori patterned thereon, and at least two protective layers, and said inner layer with its one or more sensing elements is sealably sandwiched between said two protective layers.

2. A wafer comprising an array of fluidic sensor devices according to claim 1 integrally assembled therein by attaching two or more layers one to the other, said wafer comprising a sealing sheet comprising a respective array of the sealing elements and sealably attached to a respective array of base body structures for covering their openings and placing the a priori patterned or mounted sensing elements thereover.

3. The device of claim 1 wherein the base body structure comprises at least one of the following: (i) at least one open cavity in fluid communication with the fluid channel; (ii) at least one fluid port adapted to couple to a fluid source, or to a fluid passage or reservoir, said at least one fluid port being in fluid communication with the fluid channel or cavity; and (iii) at least one fluid restrictor formed inside the fluid channel.

4. The device of claim 1 wherein the base body structure comprises first and second cavities with respective first and second openings formed in a wall thereof, each opening opens into its respective cavity and sealably covered by a portion of the sealing element comprising a respective sensing element, and a slender channel having first and second ends configured to respectively fluidly communicate with said first and second cavities, said slender channel is sealably closed by the sealing element.

5. The device of claim 1 wherein the base body structure is assembled from two or more separate body elements configured to attach one to the other and thereby form the fluid channel or cavity of said base body structure, at least one of said two or more separate body structures comprises at least one opening configured to form the at least one opening in the external face of said base body structure being in fluid communication with said fluid channel or cavity when said two or more separate body elements are attached one to the other to assemble said base body structure.

6. The device of claim 5 wherein the at least two body elements comprise at least one of the following: (i) two channel forming body elements, each of said two channel forming body elements comprises a base portion and at least one open channel extending along a length of said base portion, said at least one open channel of said channel forming body elements configured to form at least a portion of the fluid channel being in fluid communication with the at least one opening when attached one to the other; and (ii) the base portion of one of the two channel forming body elements comprises first and second cavities with respective first and second openings formed in a wall thereof, each opening opens into a respective cavity and sealably covered by a portion of the sealing element comprising a respective sensing element, and wherein at least one of the two channel forming body elements comprises a channel having first and second ends configured to respectively fluidly communicate with said first and second cavities when said body elements are attached one to the other.

7. The device of claim 6 wherein the sealing element comprises a pass through bore configured to be located over the first opening and fluidly communicate therewith to thereby form a fluid transmission passage and the second opening being sealably covered by a portion of the sealing element comprising the at least one sensing element, and wherein the at least two body elements comprises a flow transmission body element comprising an elongated open channel, said flow transmission body element configured to sealably attach over a portion of the sealing element and fluidly communicate between said fluid transmission passage and the portion of the sealing element sealably covering said second opening.

8. The device of claim 7 wherein the flow transmission body element comprises an opening formed in a wall thereof covered by a gas discharge component, said gas discharge component configured to eject gasses trapped inside the elongated channel of the flow reversing body element.

9. A fluidic sensor device comprising:
a base body structure comprising a fluid channel or cavity passing therealong and at least one opening in an external face of said base body structure and being in fluid communication with said fluid channel or cavity; and
a sealing element comprising one or more sensing elements a priori patterned or mounted thereon, said sealing element sealably attached over said external face of said base body structure comprising said at least one opening such that its one or more sensing elements become located over said at least one opening, said one or more sensing elements configured to measure at least one property or condition of a fluid substance when said fluid substance is introduced into said fluid channel or cavity and interact with a portion of said sealing element located over said at least one opening;
wherein the one or more sensing elements comprises at least one electrode positioned on an underside of the sealing element and configured to become in physical contact with the fluid substance when introduced into the fluid channel or cavity.

10. The device of claim 9 wherein the sealing element comprises at least one via for electrically coupling to the at least one electrode by means of contacts pads on the upper side of the sealing element.

11. A fluidic sensor device comprising:
a base body structure comprising a fluid channel or cavity passing therealong and at least one opening in an external face of said base body structure and being in fluid communication with said fluid channel or cavity;
a sealing element comprising one or more sensing elements a priori patterned or mounted thereon, said sealing element sealably attached over said external face of said base body structure comprising said at least one opening such that its one or more sensing elements become located over said at least one opening, said one or more sensing elements configured to measure at least one property or condition of a fluid substance when said fluid substance is introduced into said fluid channel or cavity and interact with a portion of said sealing element located over said at least one opening; and
a shielding element attached to the base body structure and a portion of the sealing element comprising the at least one sensing element and configured to prevent deformations of said portion of the sealing element.

12. A fluidic sensor device comprising:
a base body structure comprising a fluid channel or cavity passing therealong and at least one opening in an external face of said base body structure and being in fluid communication with said fluid channel or cavity;
a sealing element comprising one or more sensing elements a priori patterned or mounted thereon, said sealing element sealably attached over said external face of said base body structure comprising said at least one opening such that its one or more sensing elements become located over said at least one opening, said one or more sensing elements configured to measure at least one property or condition of a fluid substance when said fluid substance is introduced into said fluid channel or cavity and interact with a portion of said sealing element located over said at least one opening; and
a shielding element attached to the base body structure and a portion of the sealing element comprising the at least one sensing element, the shielding element comprises an open cavity configured to be placed over a portion of the sealing element covering one of the at least one opening and thereby enable deformation of said portion of the sealing element while thermally and/or physically isolating it from the external environment.

13. The device of claim 12 wherein the open cavity comprises one or more openings configured to allow entry of air from the external environment into the cavity.

14. The device of claim 12 wherein the open cavity is configured to maintain a predetermined pressure level over a portion of the sealing elements covering one of the at least one opening.

15. A method of constructing fluidic sensor device, the method comprising:
forming a base body structure comprising a fluid channel or cavity passing therealong and being in fluid communication with at least one opening in an external face of said base body structure;
constructing a sealing element having a deformable portion by sandwiching an inner layer comprising one or more a priori patterned sensing elements between at least two protective layers; and
attaching said sealing element over said external face of said base body structure comprising said at least one opening such that its one or more sensing elements become located over said at least one opening, said one or more sensing elements configured to measure at least one property or condition of a fluid substance responsive to deformations of said deformable portion, when said fluid substance is introduced into said fluid channel or cavity and interact with said deformable portion of said sealing element located over said at least one opening.

16. The method of claim 15 comprising assembling the base body structure by attaching two or more separate body elements to thereby form at least one of: (i) the fluid channel or cavity in fluid communication with the at least one opening; (ii) at least one fluid port in fluid communication with the fluid channel or cavity; and (iii) at least one fluid restrictor in the fluid channel.

17. A method of constructing a wafer integrally comprising an array of the fluidic sensor devices of claim 15, the method comprising preparing an array of body base structures, patterning or mounting on a sealing sheet an array of one or more sensing elements, and attaching the sealing sheet over said array of the base body structures so as to seal the respective at least one opening of the base body structures and place respective one or more sensing elements thereover.

18. A fluidic sensor device comprising:
a base body structure comprising a fluid channel passing therealong and at least one opening in an external face of said base body structure and being in fluid communication with said fluid channel;
at least one fluid restrictor formed inside the fluid channel; and
a sealing element comprising one or more sensing elements a priori patterned or mounted thereon, said sealing element sealably attached over said external face of said base body structure comprising said at least one opening such that its one or more sensing elements become located over said at least one opening, wherein said one or more sensing elements are configured to measure at least one property or condition of a fluid substance responsive to deformations of said deformable portion when said fluid substance is introduced into said fluid channel and interact with said sealing element located over said at least one opening.

* * * * *